US012741060B2

(12) United States Patent
Thomson et al.

(10) Patent No.: US 12,741,060 B2
(45) Date of Patent: Sep. 22, 2026

(54) GENERATING ENDOTHELIAL CELL-SEEDED VASCULAR GRAFTS

(71) Applicant: WISCONSIN ALUMNI RESEARCH FOUNDATION, Madison, WI (US)

(72) Inventors: James A. Thomson, Madison, WI (US); Jue Zhang, Madison, WI (US); John Maufort, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/830,051

(22) Filed: Jun. 1, 2022

(65) Prior Publication Data

US 2022/0296782 A1 Sep. 22, 2022

Related U.S. Application Data

(63) Continuation of application No. 16/556,674, filed on Aug. 30, 2019, now Pat. No. 11,395,866.
(Continued)

(51) Int. Cl.
*A61F 2/82* (2013.01)
*A61F 2/07* (2013.01)
(Continued)

(52) U.S. Cl.
CPC .............. *A61L 27/507* (2013.01); *A61F 2/07* (2013.01); *A61F 2/82* (2013.01); *A61L 27/56* (2013.01);
(Continued)

(58) Field of Classification Search
CPC ...... A61L 27/507; A61L 27/56; A61L 31/146; A61L 31/148; A61L 31/16;
(Continued)

(56) References Cited

U.S. PATENT DOCUMENTS 4,961,954 A * 10/1990 Goldberg .................. C08J 7/18 522/167
5,077,215 A * 12/1991 McAuslan ........... C12N 5/0068 623/920
(Continued)

FOREIGN PATENT DOCUMENTS

CN 1870948 A 11/2006
WO 1998045479 A1 10/1998
(Continued)

OTHER PUBLICATIONS

International Search Report and Written Opinion for PCT/US2019/049003, mailed Dec. 5, 2019.
(Continued)

*Primary Examiner* — Suzette J Gherbi
(74) *Attorney, Agent, or Firm* — McDonnell Boehnen Hulbert & Berghoff LLP

(57) ABSTRACT

Provided herein are human arterial endothelial cell-seeded polymeric vascular grafts suitable for replacing or bypassing natural blood vessels and exhibiting increased long term patency rates and reduced leukocyte adhesion relative to grafts comprising venous endothelial cells. Methods for generating the human arterial endothelial cell-seeded vascular grafts and therapeutic uses of the same are also described.

13 Claims, 5 Drawing Sheets

Related U.S. Application Data

(60) Provisional application No. 62/725,469, filed on Aug. 31, 2018.

(51) Int. Cl.
*A61L 27/50* (2006.01)
*A61L 27/56* (2006.01)
*A61L 31/14* (2006.01)
*A61L 31/16* (2006.01)
*C12N 5/071* (2010.01)

(52) U.S. Cl.
CPC ........... *A61L 31/146* (2013.01); *A61L 31/148* (2013.01); *A61L 31/16* (2013.01); *C12N 5/0692* (2013.01); *A61L 2300/252* (2013.01); *A61L 2300/412* (2013.01); *A61L 2300/42* (2013.01)

(58) Field of Classification Search
CPC ......... A61L 2300/252; A61L 2300/412; A61L 2300/42; A61F 2/07; A61F 2/82; C12N 5/0692
USPC ................................................ 623/1.35–1.48
See application file for complete search history.

(56) References Cited

U.S. PATENT DOCUMENTS 5,246,451 A * 9/1993 Trescony ............ A61L 33/0076 435/402
5,453,467 A * 9/1995 Bamford ................ C08L 75/16 525/422
5,522,881 A * 6/1996 Lentz ........................ A61F 2/07 623/1.13
5,609,631 A * 3/1997 Rubens ................... A61L 27/34 427/2.24
5,705,732 A * 1/1998 Sims ...................... C07K 16/18 536/23.1
5,962,620 A * 10/1999 Reich ...................... A61L 29/06 528/73
6,100,443 A * 8/2000 Sims ....................... A61L 27/38 623/23.72
6,218,371 B1 * 4/2001 Krieg ...................... A61P 31/12 514/19.5
6,537,567 B1 * 3/2003 Niklason ................ C12M 21/08 435/395
6,632,790 B1 * 10/2003 Yurchenco ............. C07K 14/78 977/915
6,916,654 B1 * 7/2005 Sims .................. A01K 67/0278 800/13
7,820,172 B1 * 10/2010 Zamora .................. C07K 14/78 530/328
7,906,116 B2 * 3/2011 Gill ......................... A61P 17/00 424/178.1
8,642,072 B2 2/2014 Coffey et al.
8,808,687 B2 8/2014 Humayun et al.
8,889,179 B2 11/2014 Coffey et al.
9,133,266 B2 9/2015 Thomson et al.
9,855,131 B2 * 1/2018 Pathak ...................... A61F 2/06
11,376,123 B2 * 7/2022 Gründeman .......... A61F 2/2412
11,395,866 B2 * 7/2022 Thomson .............. A61L 31/148
11,786,639 B2 * 10/2023 Turng ................... A61L 27/507 424/426
2003/0139364 A1 * 7/2003 Krieg ..................... A61K 39/39 435/7.1
2004/0044403 A1 3/2004 Bischoff et al.
2006/0083770 A1 * 4/2006 Greiner ................... A61L 31/10 427/2.26
2007/0128171 A1 6/2007 Tranquillo et al.
2008/0171385 A1 7/2008 Bergendahl et al.
2008/0299168 A1 * 12/2008 Dadey .................... A61K 47/12 424/78.37
2009/0082856 A1 * 3/2009 Flanagan ................ A61L 31/10 623/1.49
2011/0213127 A1 * 9/2011 Gill ........................ C07K 16/22 530/387.3
2014/0134195 A1 5/2014 Russell
2014/0271583 A1 9/2014 Allen-Hoffmann et al.
2015/0164642 A1 * 6/2015 Khosravi ............ A61M 25/104 623/1.25
2016/0022452 A1 * 1/2016 Cottone .................. A61L 27/18 623/1.16
2016/0081788 A1 * 3/2016 Pathak .................... B29C 48/00 623/1.42
2016/0244719 A1 * 8/2016 Thomson ............. C12N 5/0056
2017/0306292 A1 10/2017 Dahl et al.
2020/0246126 A1 * 8/2020 Wang .................... A61L 27/507
2021/0060208 A1 * 3/2021 Hoerstrup ........... A61L 27/3641
2022/0008190 A1 * 1/2022 Lu ........................... A61L 27/48
2022/0152273 A1 * 5/2022 Kyriakides ............. A61L 33/18
2022/0162412 A1 * 5/2022 Chian ..................... A61L 27/60
2022/0211920 A1 * 7/2022 Gu ......................... A61L 31/047
2023/0191005 A1 * 6/2023 Hall ...................... A61L 31/146 424/443

FOREIGN PATENT DOCUMENTS

WO 2009103012 A1 8/2009
WO WO-2015128826 A1 * 9/2015 ........... A61B 5/1459
WO WO-2016134313 A1 * 8/2016 ............. A61K 35/44

OTHER PUBLICATIONS

De Charette, M. and Houot, R. Hide or defend, the two strategies of lymphoma immune evasion: potential implications for immunotherapy. Haematologica. Aug. 2018;103(8):1256-1268. doi: 10.3324/haematol. 2017.184192. Epub Jul. 13, 2018. PMID: 30006449; PMCID: PMC6068015.

Teo et. al., Polymeric Biomaterials for Medical Implants and Devices. ACS Biomater. Sci. Eng. 2016, 2, 454-472. Feb. 16, 2016.

Bensen, CV., et al. (1991). Quantification of gas denucleation and thrombogenicity of vascular grafts. Journal of biomedical materials research 25, 373-386.

Berridge, M. J., et al. "Neural and developmental actions of lithium: a unifying hypothesis." Cell 59.3 (1989):111-419.

Challa-Malladi, M., et al. "Combined genetic inactivation of b2-Microglobulin and CD58 reveals frequent escape from immune recognition in diffuse large B cell lymphoma." Cancer cell 20.6 (2011): 728-740.

Chen, G. et al. "Chemically defined conditions for human iPSC derivation and culture." Nature methods 8.5 (2011): 424.

Chlupác, J. et al. "Attachment of human endothelial cells to polyester vascular grafts: pre-coating with adhesive protein assemblies and resistance to short-term shear stress." Physiological research 63.2 (2014).

De Caterina, R. et al. (1995). Nitric oxide decreases cytokine-induced endothelial activation. Nitric oxide selectively reduces endothelial expression of adhesion molecules and proinflammatory cytokines. J Clin Invest 96, 60-68.

De Rham, C. et al. "Potential and limitation of HLA-based banking of human pluripotent stem cells for cell therapy." Journal of immunology research 2014 (2014).

Deuse, T. et al. "Hypoimmunogenic derivatives of induced pluripotent stem cells evade immune rejection in fully immunocompetent allogeneic recipients." Nature biotechnology 37.3 (2019): 252.

Deutsch, M. et al. "Long-term experience in autologous in vitro endothelialization of infrainguinal ePTFE grafts." Journal of vascular surgery 49.2 (2009): 352-362.

Deutsch, M. et al. (1999). Clinical autologous in vitro endothelialization of infrainguinal ePTFE grafts in 100 patients: a 9-year experience. Surgery 126, 847-855.

Ebert, A. D. et al. "Induced pluripotent stem cells from a spinal muscular atrophy patient." Nature 457.7227 (2009): 277.

Gabbieri, D. et al. "Aortocoronary endothelial cell-seeded polytetrafluoroethylene graft: 9-year patency." The Annals of thoracic surgery 83.3 (2007): 1166-1168.

(56) References Cited

OTHER PUBLICATIONS

Gornalusse, G. G., et al. "HLA-E-expressing pluripotent stem cells escape allogeneic responses and lysis by NK cells." Nature biotechnology 35.8 (2017): 765.
Ha, S. Y. et al. "Cryopreservation of human embryonic stem cells without the use of a programmable freezer." Human reproduction. 20.7 (2005): 1779-1785.
Hayflick, L. "The limited in vitro lifetime of human diploid cell strains." Experimental cell research 37.3 (1965): 614-636.
Howden, S. E., et al. "Genetic correction and analysis of induced pluripotent stem cells from a patient with gyrate atrophy." Proceedings of the National Academy of Sciences 108.16 (2011): 6537-6542.
Inman, G. J. et al. "SB-431542 is a potent and specific inhibitor of transforming growth factor-b superfamily type I activin receptor-like kinase (ALK) receptors ALK4, ALK5, and ALK7." Molecular pharmacology 62.1 (2002): 65-74.
Kirkton, R. D. et al. "Bioengineered human acellular vessels recellularize and evolve into living blood vessels after human implantation." Science translational medicine 11.485 (2019): eaau6934.
Legein, B. et al. (2013). Inflammation and immune system interactions in atherosclerosis. Cell Mol Life Sci 70, 3847-3869.
Lu, B. et al. "Long-term safety and function of RPE from human embryonic stem cells in preclinical models of macular degeneration." Stem cells 27.9 (2009): 2126-2135.
Meinhart, J. et al. (1997). Eight years of clinical endothelial cell transplantation. Closing the gap between prosthetic grafts and vein grafts. ASAIO J 43, M515-521.
Riolobos, L. et al. "HLA engineering of human pluripotent stem cells." Molecular Therapy 21.6 (2013): 1232-1241.
Rufaihah, A. J. et al. "Endothelial cells derived from human iPSCS increase capillary density and improve perfusion in a mouse model of peripheral arterial disease." Arteriosclerosis, thrombosis, and vascular biology 31.11 (2011 ): e72-e79.
Shutter, J. R., et al. "D114a, novel Notch ligand expressed in arterial endothelium." Genes & development 14.11 (2000): 1313-1318.
Taylor, C. J. et al. "Generating an iPSC bank for HLA-matched tissue transplantation based on known donor and recipient HLA types." Cell stem cell 11.2 (2012): 147-152.
Thomson, J. A. et al. "Embryonic stem cell lines derived from human blastocysts." Science 282.5391 (1998): 1145-1147.
Torikai, H. et al. "Toward eliminating HLA class I expression to generate universal cells from allogeneic donors." Blood 122.8 (2013): 1341-1349.
Yu, J. et al. "Human induced pluripotent stem cells free of vector and transgene sequences." Science 324.5928 (2009): 797-801.
Yu, J. et al. "Induced pluripotent stem cell lines derived from human somatic cells." science 318.5858 (2007): 1917-1920.
Zhang, J. et al. (2017). Functional characterization of human pluripotent stem cell-derived arterial endothelial cells. Proceedings of the National Academy of Sciences of the United States of America 114, E6072-e6078.
Zilla, P. et al. (1989). Use fibrin glue as a substrate for in vitro endothelialization of PTFE vascular grafts. Surgery 105, 515-522.
Zimmerman, A. et al. "Haplotype-based banking of human pluripotent stem cells for transplantation: potential and limitations." Stem cells and development 21.13 (2012): 2364-2373.

* cited by examiner

GENERATING ENDOTHELIAL CELL-SEEDED VASCULAR GRAFTS

CROSS-REFERENCE TO RELATED APPLICATIONS

This application is a continuation of U.S. application Ser. No. 16/556,674, filed Aug. 30, 2019, which claims the benefit of priority to U.S. Application No. 62/725,469, filed Aug. 31, 2018, which is are incorporated herein by reference as if set forth in its their entirety.

STATEMENT REGARDING FEDERALLY FUNDED RESEARCH OR DEVELOPMENT

This invention was made with government support under HL134655 awarded by the National Institutes of Health. The government has certain rights in the invention.

BACKGROUND

A frequent procedure in cardiovascular surgery is to replace or bypass a blood vessel in order to provide more adequate flow of blood to downstream tissues. In coronary artery bypass operations, arterial grafts have much better long term patency rates than venous grafts. If the operation requires multiple grafts, however, veins are often used because the patient lacks suitable additional arterial grafts. In bypass operations to treat peripheral artery disease, the arteries to be bypassed are generally so large that no suitable arterial grafts are available. Again, vein grafts are often used in spite of the comparatively high long-term rate of occlusion.

Many significant disadvantages are associated with transplantation of a patient's own vessels for bypass operations. The time required to excise the vessel and prepare it for transplant increases the patient's exposure to anesthesia, increases the chance of postoperative infection, and increases the cost of the procedure. For many patients, suitable arteries or veins are simply not available for grafting due to vascular disease or prior surgeries.

Because of the limitations of using a patient's own vessels as grafts, there have been numerous attempts at making vascular grafts from synthetic materials. While synthetic grafts generally work well for treatments involving the largest diameter vessels (e.g., the aorta), long term patency rates for synthetic grafts decrease as vessel size decreases. For peripheral artery disease of the leg, artificial grafts are used as a last resort when a suitable vein graft is not available, because artificial grafts in this location occlude at a higher rate than vein grafts. For bypass operations involving even smaller cardiac arteries (~3-5 mm diameter vessels), synthetic grafts fail at such a high rate that they are not currently used.

One group has found that by lining a synthetic ePTFE material with a patient's own venous endothelial cells, they could improve long term patency rates of ePTFE grafts in peripheral arterial disease to approximately equal the long term patency rates of venous grafts (Deutsch et al., 1999). This procedure, however, requires harvesting a patient's vein in a separate surgery, expanding the venous endothelial cells in culture, lining the ePTEE tube with the venous endothelial cells, maturing the cells on the ePTFE during extended culture, and then finally transplanting the ePTFE/venous endothelial cell graft back to the patient. The entire procedure from vein harvest to transplant takes about a month (Deutsch et al., 2009). Thus, the procedure is expensive and slow. About ⅓ of the patients with peripheral artery disease have an acute need for intervention and cannot wait 30 days—the time necessary for production of the ePTFE/autologous venous endothelial cell graft. And because of immune rejection, this approach can only treat an individual patient and cannot be scaled up for the treatment of multiple patients. Finally, although the improvement in patency rates of venous endothelial cell-lined ePTFE grafts over standard ePTFE grafts was impressive, those rates still only approach the long term patency rates of vein grafts, not arterial grafts.

Arterial endothelial cells differ from venous endothelial cells in key biological properties, such as lower leukocyte adhesion and higher nitric oxide (NO) production, which are critical for maintaining the long-term patency of vascular grafts. Harvesting primary arterial endothelial cells from the patient is not medically feasible, and primary arterial endothelial cells undergo de-differentiation upon in vitro culture, so polymeric grafts lined with arterial endothelial cells have never been used clinically. Accordingly, there remains a need in the art for improved polymeric vascular grafts comprising arterial endothelial cells that are scalable, available as on-demand products, and suitable for multiple patients.

SUMMARY OF THE DISCLOSURE

In a first aspect, provided herein is a vascular graft comprising or consisting essentially of (a) a polymeric substrate at least partially coated by an endothelial cell attachment agent and (b) human arterial endothelial cells adhered to said coated polymeric substrate. The polymeric substrate can be selected from expanded polytetrafluoroethylene (ePTFE), poly vinyl chloride (PVC), PGA (poly glycolic acid), PLA (poly lactic acid), PCL (poly caprolactone), PGLA (polylactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracelluar matrix protein-based scaffold, hyaluronic acid, chitosan, and polyhydroxyalkanoate. The endothelial cell attachment agent can comprise one or more of dopamine, fibrin glue, RGD peptides, vitronectin, and laminin. The vascular graft can exhibit reduced leukocyte adhesion relative to a polymeric substrate seeded with venous endothelial cells. The vascular graft can exhibit one or more of (a) reduced thrombosis, (b) increased long-term patency, and (c) reduced platelet adherence, relative to a polymeric substrate not coated with human arterial endothelial cells. The human arterial endothelial cells can be produced from human pluripotent stem cells. The human pluripotent stem cells can be induced pluripotent stem cells. The induced pluripotent stem cells can be autologous to the patient. The induced pluripotent stem cells can be at least 50% HLA matched to the patient. The human arterial endothelial cells can be non-immunogenic to a recipient of the vascular graft. The human arterial endothelial cells can comprise one or more genetic modifications such that they do not express a beta2-microglobulin gene. The human arterial endothelial cells can comprise one or more genetic modifications such that they do not express one or more proteins encoded by class I or class II major histocompatibility complex (MHC) genes. The human arterial endothelial cells can comprise one or more genetic modifications such that they do not express CD58 polypeptide. The human arterial endothelial cells can comprise one or more modifications such that they over-express one or both of HLA-E (Edimer) and CD47.

In another aspect, provided herein is a method of forming a cell-seeded vascular graft, the method comprising or consisting essentially of (a) coating a polymeric substrate with an endothelial cell attachment agent; (b) seeding human arterial endothelial cells onto the coated polymeric substrate; and (c) culturing the seeded, coated polymeric substrate for about 2 to about 20 days, whereby a cell-seeded vascular graft is obtained. The method can further comprise de-gassing the polymeric substrate prior to coating with one or more endothelial cell attachment agents. De-gassing can comprise washing the polymeric substrate in acetone and ethanol, washing the polymeric substrate in an organic solvent, or applying a vacuum. The polymeric substrate can be selected from expanded polytetrafluoroethylene (ePTFE), poly vinyl chloride (PVC), PGA (poly glycolic acid), PLA (poly lactic acid), PCL (poly caprolactone), PGLA (poly-lactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracelluar matrix protein-based scaffold, hyaluronic acid, chitosan, and polyhydroxyalkanoate. The method can further comprise contacting the cell-seeded vascular graft to a cryopreservation solution and freezing the contacted cell-seeded vascular graft. Freezing can comprise storage at a temperature from 1° C. to about −196° C.

In a further aspect, provided herein is a method of fabricating an AEC cell-seeded vascular graft vascular graft, the method comprising or consisting essentially of coating at least a portion of a polymeric substrate with one or more endothelial attachment agents; and contacting human arterial endothelial cells to the coated polymeric substrate, thereby forming an AEC-seeded vascular graft which is substantially non-adhesive to leukocytes or cellular fragments thereof. The polymeric substrate can be selected from expanded polytetrafluoroethylene (ePTFE), poly vinyl chloride (PVC), PGA (poly glycolic acid), PLA (poly lactic acid), PCL (poly caprolactone), PGLA (polylactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracelluar matrix protein-based scaffold, hyaluronic acid, chitosan, and polyhydroxyalkanoate. The method can further comprise de-gassing the polymeric substrate prior to coating with one or more endothelial cell attachment agents. De-gassing can comprise washing the polymeric substrate in acetone and ethanol, washing the polymeric substrate in an organic solvent, or applying a vacuum.

These and other features, aspects, and advantages of the present invention will become better understood from the description that follows. In the description, reference made to preferred embodiments is not intended to limit the invention. Reference should therefore be made to the claims recited herein for interpreting the scope of the invention.

BRIEF DESCRIPTION OF THE DRAWINGS

The following drawings form part of the present specification and are included to further demonstrate certain aspects of the compositions and methods provided herein. The invention may be better understood by reference to one or more of these drawings in combination with the detailed description of specific embodiments presented herein.

DETAILED DESCRIPTION OF THE DISCLOSURE

Figures 1A, 1B:
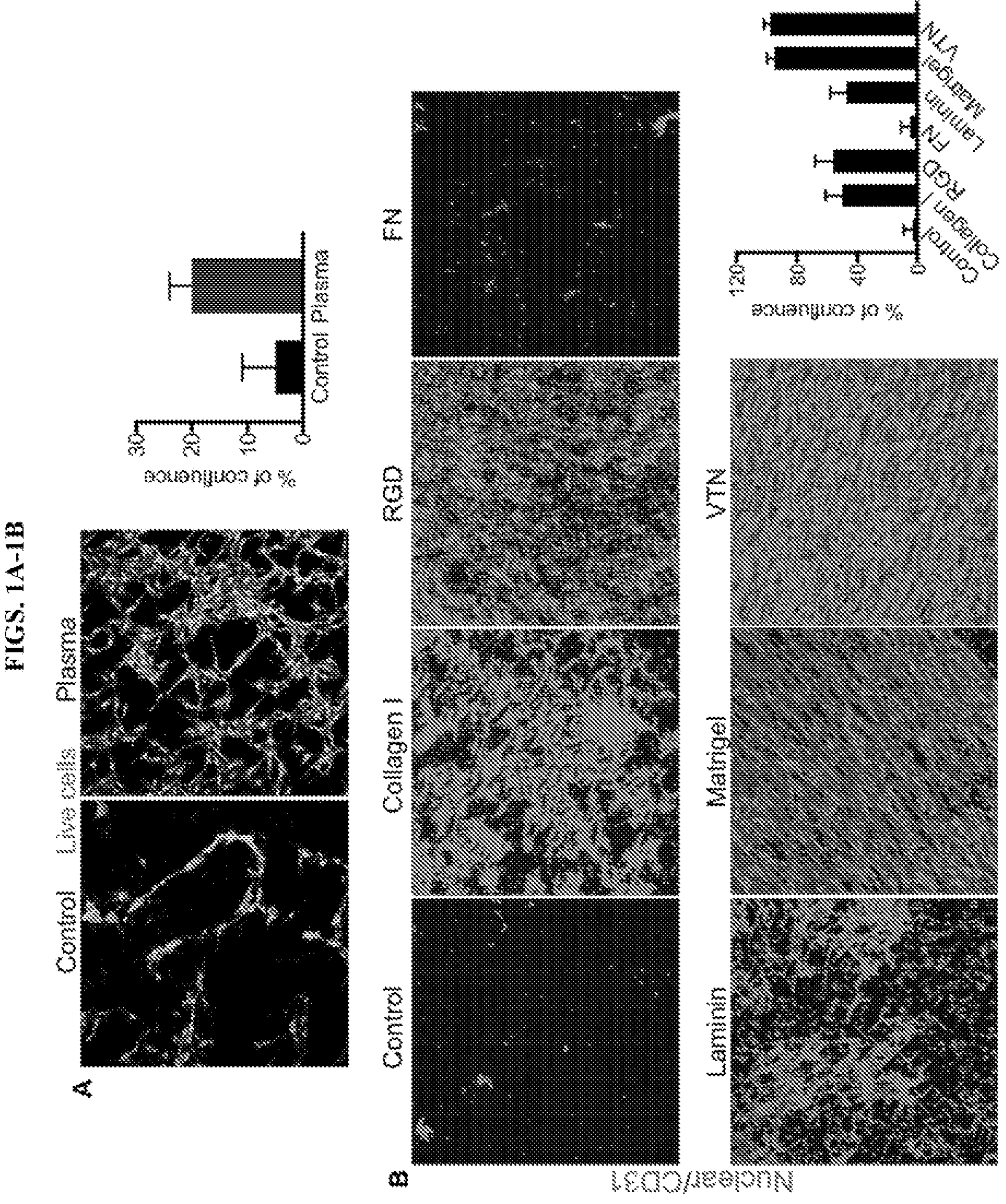
FIGS. 1A-1B are images showing $CD3V^+$ AECs seeded on adhesion agent-coated expanded polytetrafluoroethylene (ePTFE). (A) AECs were seeded on ePTFE at a cell density between $1\times10^6$ cells/mi and $1.5\times10^6$ cells/mi. Staining was performed to detect live cells (green; stained with cell-permeant dye calcein AM). Statistics data of cell confluency are represented as mean±SD. n=3. (B) CD31 (red) AECs seeded on ePTFE coated with Collagen I, RGD (Arg-Gly-Asp) peptides, Fibronectin (FN), laminin, Matrigel, and VTN (vitronectin). DAPI (4',6-diamidino-2-phenylindole) fluorescent stain was used to visualize nuclei. Statistics data of cell confluency are represented as mean±SD. n=3.

All publications, including but not limited to patents and patent applications, cited in this specification are herein incorporated by reference as though set forth in their entirety in the present application.

The present invention is based, at least in part, on the inventors' development of polymeric vascular grafts seeded with arterial endothelial cells, where the vascular grafts and methods of obtaining them are scalable, available as on-demand products, and suitable for a variety of patients.

I. Compositions

In a first aspect, provided herein is a polymeric vascular graft comprising arterial endothelial cells. The graft can comprise or consist essentially of a polymeric substrate at least partially coated by an endothelial cell attachment agent, and arterial endothelial cells (AECs) adhered to coated polymeric substrate. As described herein, AEC-seeded polymeric grafts of this disclosure exhibit increased patency relative to conventional polymeric vascular grafts. In some cases, human arterial endothelial cells used with the polymeric vascular grafts of this disclosure are modified such that they can serve as universal donor cells for transplant into a subject in need thereof regardless of the HLA- and blood group type of the graft recipient. For example, in some embodiments, the cell's natural genome is engineered such that the engineered cell does not express certain cell surface markers such as proteins encoded by either the class II or both the class I and the class II major histocompatibility complex genes. In this way, the genetically engineered cells are more likely to evade attack by T-cells of the graft recipient and, thus, are non-immunogenic to the recipient.

The terms "graft" and "vascular graft" are used interchangeably herein and refer to any conduit or portion thereof intended as a prosthetic device for conveying fluid (e.g., blood) and therefore having a fluid-contacting (i.e., "luminal") surface. While it is intended primarily as a tubular form, the graft may also be a partial tube or sheet material useful for patching portions of the circumference of living blood vessels (these materials are generally referred to as cardiovascular patches). Likewise, the term vascular graft includes intraluminal grafts for use within living blood vessels. For example, vascular grafts provided herein may be used as a sheath or other covering on the exterior surface, luminal surface, or both luminal and exterior surfaces of an implantable vascular stent.

As used herein, the term "AEC seeded" and grammatical variations thereof refer to a substrate upon which arterial endothelial cells are provided. Preferably, the term refers to polymeric vascular grafts bearing arterial endothelial cells (e.g., human AECs) and an endothelial cell adhesion agent, whereby the seeded polymeric vascular graft is suitable for implantation into a subject.

As used herein, the term "patency" refers to the degree of openness of a tube, such as a blood vessel or vascular graft. A vascular graft having 100% patency is free of any blockage or obstruction. As the degree of blockage or obstruction increases, patency of the vessel or vascular graft decreases. In this manner, patency of a vessel or vascular graft is a proxy for graft success or failure. In some cases, patency is assessed at a particular time point including, without limitation, patency of a vascular graft days, weeks, months, or years following implantation. Preferably, polymeric vascular grafts of this disclosure exhibit increased long-term patency rates relative to conventional polymeric vascular grafts. As used herein, "long-term patency" means a vessel or graft remains patent in a physiological environment for more than 1 year, preferably more than 3 years, more preferably more than 5 years, and most preferably 10 years or more following implantation. In some cases, AEC-seeded polymeric vascular grafts of this disclosure exhibit patency that matches and, preferably, outperforms autologous grafts.

A. Materials for Compositions

Polymeric vascular grafts provided herein comprise a polymeric substrate at least partially coated by an endothelial cell attachment agent, and human arterial endothelial cells adhered to said coated polymeric substrate. Suitable polymeric materials for the vascular grafts provided herein include, without limitation, poly vinyl chloride (PVC), PGA (poly glycolic acid), PLA (poly lactic acid), PCL (poly caprolactone), polylactic-co-glycolic acid (PLGA), polyurethane, polydioxanone, polyethylene terephthalate (Dacron®), polyethylene, and fluoropolymers such as tetrafluoroethylene (TFE), polytetrafluoroethylene (PTFE), and expanded polytetrafluoroethylene (ePTFE). PTFE is a homopolymer of tetrafluoroethylene (TFE). When PTFE is stretched and expanded into ePTFE, the polymeric material is particularly suitable for vascular applications as it exhibits low thrombogenicity and can be extruded as a tube, sheet, or other suitable graft shape. In some cases, the polymeric substrate is a GORE-TEX® vascular graft.

In some cases, biological materials are suitable for polymeric substrates of this disclosure. For example, polymeric substrates can comprise biological materials including, without limitation, silk, a decellularized construct (such as decellularized artery, vein, or small intestine), an extracelluar matrix protein-based scaffold (such as collagen, MATRIGEL™, fibrin, elastin), hyaluronic acid, chitosan, polyhydroxyalkanoates In some cases, polymeric substrates used for the vascular grafts provided herein are biocompatible, which means that the substrate material will not cause adverse reactions when implanted or placed in contact with the body.

In some cases, the polymeric substrate is a porous substrate. Without being bound to any mode of action or theory, it is believed that pores in the polymeric vascular grafts allow for recruitment and integration of host cells into the graft. For example, ePTFE exhibits high porosity and comprises a matrix of nodes and fibrils. The fibrils are thin connections between the nodes and are submicron in size. Thin fibrils are used to create more tortuosity and surface area in a membrane, impacting the filtration efficiency. In some cases, the geometry of fibrils and nodes in the membrane is modified (e.g., increasing or decreasing pore size(s), pore distribution) to customize the material's functionality. In some cases, an intermodal distance of about 7 μm to about 20 μm is preferred. In some cases, the polymeric substrate is microporous, meaning that pores of the porous substrate have micrometer scale sizes. Preferably, pore sizes of suitable polymeric substrates are within, and preferably cover, the range of 2 micron to 80 micron, preferably in the range from 3 micron to 40 micron, most preferably in the range from 5 micron to 35 micron, in particular around 30 micron.

In some cases, the disclosed vascular grafts are substantially tubular in shape with a round or substantially round cross-section.

The disclosed vascular grafts are substantially tubular in shape with a round or substantially round cross-section. In some cases, the tubular structure has a wall thickness of about 200 μm to about 500 μm (e.g., about 200, 250, 300, 350, 400, 450, 500 μm). In other cases, the polymeric substrate is a planar sheet or "patch" of polymeric material. In such cases, the thickness may vary widely from about 0.2 mm to about 1.0 mm or more.

The various dimensions of a polymeric vascular graft of this disclosure may vary according to the desired use. In principle, the dimensions will be similar to those of the host tissue in which the vascular graft is being used to replace. Generally, tubular grafts have a lumen extending throughout the length of the graft. The lumen of a vascular graft provided herein may be of any appropriate diameter that is suitable for the intended surgical use of the graft. For instance, average luminal dimensions of coronary arteries, including those having a higher incidence of occlusions (anterior interventricular artery, right coronary artery, circumflex artery) are well described in the literature. In some cases, the polymeric substrate has an inner diameter of about 0.5 mm to about 10 mm (e.g., about 0.5, 0.75, 1, 2, 3, 4, 5, 6, 7, 8, 9, 10 mm). The vascular grafts may be of any appropriate length that is suitable for the intended surgical use of the graft Typically, the graft should be slightly longer than the length of artery or vein that is to be replaced.

In some cases, polymeric substrates used for the vascular grafts provided herein are hydrophobic membranes, meaning that they resist wetting by fluids (e.g., biological fluids) and are not chemically changed or degraded by biological fluids. In some cases, the hydrophobic membrane is impermeable to fluids but permit gas flow through the membrane.

Figures 2A, 2B, 2C, 2D:
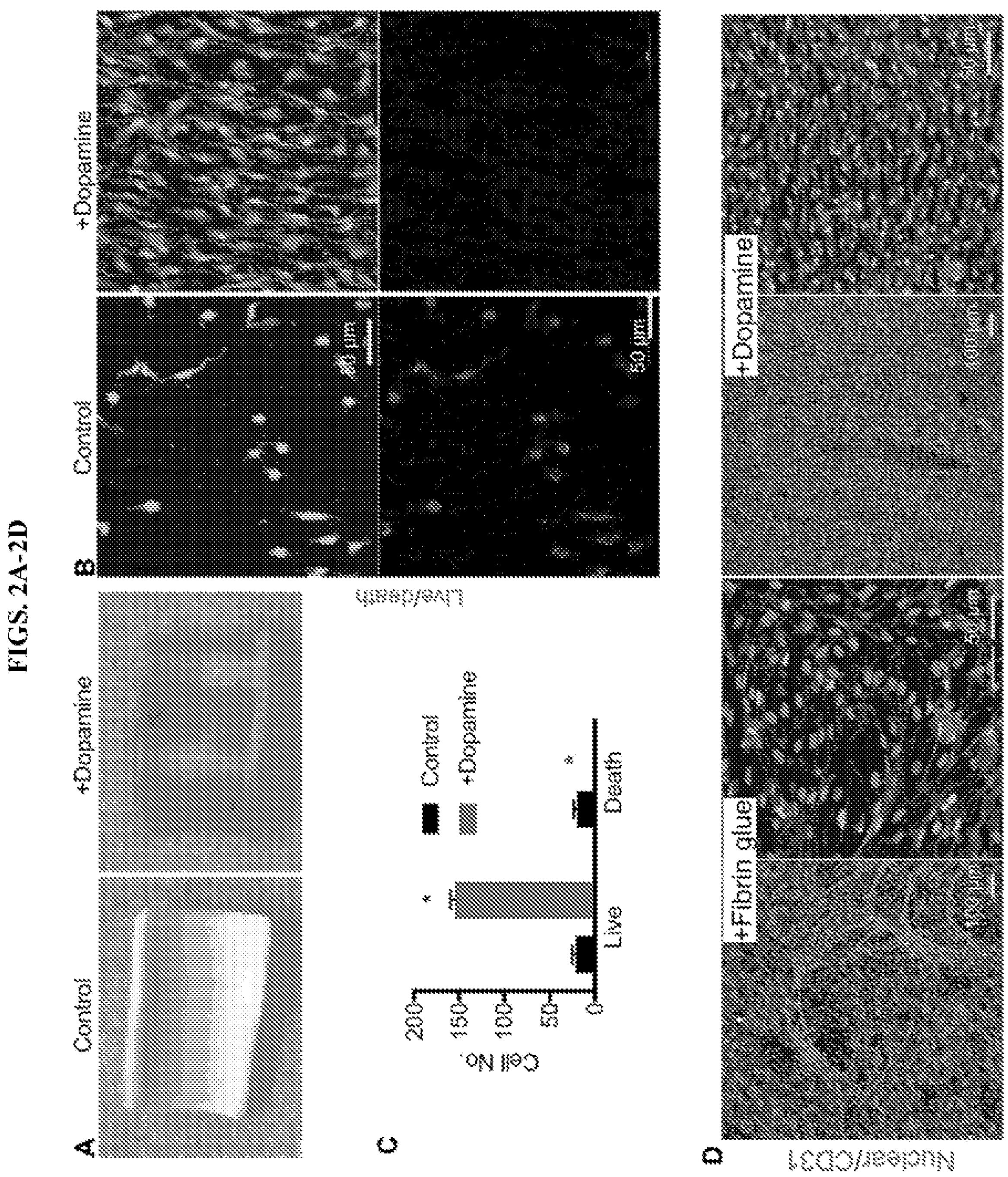
FIGS. 2A-2D demonstrate that dopamine coating improves adhesion of human arterial endothelial cells (AECs) to expanded polytetrafluoroethylene (ePTFE) substrates. (A) ePTFE with or without dopamine coating. (B) AECs were seeded on ePTFE at a cell density between $1\times10^6$ cells/ml and $1.5\times10^6$ cells/ml. Staining was performed to detect and count live cells (green; stained with cell-permeant dye calcein AM) and dead cells (red; stained with nucleic acid stain ethidium homodimer-1). (C) Statistics of live and dead AECs on control and dopamine-coated substrates. Data are represented as mean±SD. *: P<0.05, n=3. (D) Comparison of AEC adhesion on ePTFE coated with dopamine and fibrin glue.

In some cases, the polymeric substrate is at least partially coated by an endothelial cell adhesion agent. Endothelial cell adhesion agents useful for the vascular grafts of this disclosure include, without limitation, dopamine, fibrin, RGD (Arg-Gly-Asp)-peptides, and extracellular matrix proteins such as vitronectin and laminin, or mixtures of two or more adhesion agents. Conventionally, a network of blood coagulation protein fibrin (Fb) (sometimes referred to as "fibrin adhesive" or "fibrin glue") has been used to coat vascular grafts. For example, Zilla et al. (1989) described improved venous endothelial cell seeding on ePTFE using fibrin glue. However, fibrin glue methods involve multiple steps and, thus, are challenging to scale up for clinical applications. Referring to FIG. 2A-2B, the inventors demonstrated that other cell adhesion agents can achieve comparable levels of AEC adhesion on polymeric substrates. Advantageously, coating polymeric substrates with these agents requires a single step. Others have reported improved venous endothelial attachment to vascular prostheses coated with laminin relative to those coated with Fb ($p<0.001$) or with a mixture of fibrin and fibronectin ($p<0.05$). See Chlupac et al., *Physiol. Res.* 63:167-177, 2014.

Preferably, the endothelial cell adhesion agent is non-immunogenic. For example, an endothelial cell adhesion agent preferably does not comprise any component derived from a non-human animal and is, thus, free of xenogeneic material ("xeno-free"). As used herein, the terms "free of xenogeneic materials" and "xeno-free" are used interchangeably and refer to materials (e.g., cell substrate, culture medium) or cell culture conditions that are free of any cell or cell product of species other than that of the cultured cell or the recipient of the materials.

In some cases, the endothelial cell adhesion agent comprises dopamine, where the dopamine is dissolved in a buffered solution at a concentration of about 0.1 mg/ml to about 20 mg/ml (e.g., about 0.1, 0.2, 0.3, 0.4, 0.5, 0.6, 0.7, 0.8, 0.9, 1, 1.5, 2, 2.5, 3, 4, 5, 6, 7, 8, 9, 10, 12, 14, 16, 18, 20 mg/ml dopamine). Where the endothelial cell adhesion agent comprises RGD peptides, the peptides can be provided in a buffered solution at a concentration of about 0.5 mM to about 10 mM (e.g., about 0.5, 0.6, 0.7, 0.8, 0.9, 1, 2, 3, 4, 5, 6, 7, 8, 9, 10 mM RGD peptide). In some cases, the endothelial cell adhesion agent comprises vitronectin. In some cases, vitronectin is provided in a buffered solution at a concentration of about 1 μg/ml to about 50 μg/ml (e.g., about 1, 2, 5, 10, 15, 20, 25, 30, 35, 40, 45, 50 μg/ml vitronectin). As used herein, the term "vitronectin" refers to a vitronectin polypeptide or fragment or peptide thereof, and encompasses recombinant vitronectin polypeptides and peptides (e.g., recombinant human vitronectin) and vitronectin polypeptide variants such as those described by U.S. Pat. No. 9,133,266, incorporated herein by reference as if set forth in its entirety. In some cases, the endothelial cell adhesion agent comprises laminin. In some cases, laminin is provided in a buffered solution at a concentration of about 1 μg/ml to about 50 μg/ml (e.g., about 1, 2, 5, 10, 15, 20, 25, 30, 35, 40, 45, 50 μg/ml laminin). As used herein, the term "laminin" refers to a laminin polypeptide or fragment or peptide thereof, and encompasses recombinant laminin polypeptides and peptides (e.g., recombinant human laminin).

In some cases, the polymeric substrate can be partially or fully coated by or immersed in a solution comprising the endothelial cell adhesion agent for about 4 to about 24 hours. Coating by immersion in the endothelial cell adhesion agent solution can occur at any appropriate temperature including, without limitation, at 4° C., 25° C. (room temperature), or 37° C. Preferably, coated polymeric substrates are rinsed with distilled water or a buffered solution prior to use.

In some cases, it is advantageous to de-gas the polymeric substrate material prior to coating at least partially with an endothelial cell adhesion agent. As described in the Examples that follow, the inventors demonstrated reduced cell aggregate formation, improved cell density, and improved coating with endothelial adhesion agents when polymeric substrates were de-gassed before use. De-gassing can be performed by well-known methods in the art. As described in the Example, the polymeric substrate can be de-gassed in a series of acetone and ethanol washes. In some cases, de-gassing is performed as described but using an organic solvent in place of acetone. In other cases, high powered vacuum can be applied to the substrate to de-gas prior to use.

In some cases, arterial endothelial cells are seeded onto coated (e.g., partially or fully coated), degassed polymeric substrates at a cell density of about $0.5\times10^6$ cells/ml to about $3\times10^6$ cells/ml. In some cases, AECs at a density of about $1\times10^6$ to about $1.5\times10^6$ cells/mi are seeded onto a prepared polymeric substrate.

AECs can be provided in any appropriate cell culture medium for seeding polymeric substrates. For example, AECs can be provided in a chemically defined cell culture medium that is xeno-free, serum-free, and albumin-free. As used herein, the terms "chemically defined culture conditions," "fully defined, growth factor free culture conditions," and "fully defined conditions" indicate that the identity and quantity of each medium ingredient is known and the identity and quantity of supportive surface is known. As used herein, "serum-free" means that a medium does not contain serum, or that it contains essentially no serum. For example, an essentially serum-free medium can contain less than about 1%, 0.9%, 0.8%, 0.7%, 0.6%, 0.5%, 0.4%, 0.3%, 0.2% or 0.1% serum. As used herein, the term "albumin-free" indicates that the culture medium used contains no added albumin in any form (such as in serum replacement), including without limitation Bovine Serum Albumin (BSA) or any form of recombinant albumin. Preferably, human AECs are seeded onto a polymeric substrate in a chemically defined cell culture medium that is free of any xenogeneic materials, that is to say free of any components derived from a non-human animal.

In some cases, seeding is performed by injecting a suspension of AECs into the lumen of a tubular vascular graft and placing the graft in a rotating device. In some cases, seeding is followed by maturation of the seeded substrate in culture flasks with fresh medium without rotation at any temperature suitable for cell growth such as, for example, at room temperature or preferably at 37° C. For example, seeding is, in some cases, followed by 2-3 days of maturation in culture flasks with fresh culture medium without rotation in a humid incubator at 37° C. In some cases, AEC-seeded grafts are cultured under in the presence of 5% $CO_2$.

It may be appropriate, in some cases, to include a Rho-Kinase (ROCK) inhibitor in the cell culture medium for seeding polymeric substrates with AECs. Kinase inhibitors, such as ROCK inhibitors, are known to increase plating efficiency and viability of single cells and small aggregates of cells. See, e.g., US Patent Application Publication No. 2008/0171385, incorporated herein by reference as if set forth in its entirety; and Watanabe K, el al., "A ROCK inhibitor permits survival of dissociated human embryonic stem cells," *Nat. Biotechnol.* 25:681-686 (2007). ROCK inhibitors suitable for use herein include, but are not limited to, (S)-(+)-2-methyl-1-[(4-methyl-5-isoquinolinyl)sulfonyl] homopiperazine dihydrochloride (informal name: H-1152), 1-(5-isoquinolinesulfonyl)piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino) ethyl-5-isoquinoline-sulfonamide dihydrochloride (informal name: 11-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl)cyclohexanecarboxamide dihydrochloride (informal name: Y-27632). The kinase inhibitor can be provided at a concentration sufficiently high that the cells survive and remain attached to the surface. When included in an AEC culture medium, the ROCK inhibitor concentration can be about 3 IN to about 10 μM (e.g., about 3, 4, 5, 6, 7, 8, 9, 10 μM Y-27632).

B. Cells for Compositions

Since harvesting primary arterial endothelial cells from a patient in need of a cardiovascular intervention is not medically feasible and primary arterial endothelial cells de-differentiate in culture, polymeric grafts lined with arterial endothelial cells have never been used clinically. Accordingly, the AEC-seeded polymeric grafts provided herein are superior to previously described cell-seeded vascular prostheses AECs are distinguishable from other cell types, including venous endothelial cells and endothelial progenitor cells, on the basis of characteristic expression profiles and functional attributes of the cells in vitro as described herein. In particular, arterial endothelial cells exhibit distinct physiological properties that are adapted to the high flow, high pressure environment of arteries and distinguish them from venous endothelial cells. As compared to venous endothelial cells, arterial endothelial cells produce higher levels of nitrous oxide, respond more robustly to shear stress, exhibit higher metabolic rates, and adhere leukocytes poorly. See, e.g., U.S. Patent Pub. 2016/0244719, which is incorporated herein by reference in its entirety. The reduced ability of leukocytes to attach to arterial endothelial cells as compared to venous endothelial cells is particularly important because inflammation and the resulting proliferation of myointimal cells are significant contributing factors to graft occlusion (i.e., loss of patency) and failure These and other distinctive properties of arterial endothelial cells make them more suitable than venous endothelial cells for seeded polymeric arterial grafts and improving long term patency rates, but because of lack of availability, no one to date has been able to use them for that purpose clinically. The process of harvesting arteries is much more invasive than vein harvesting. In addition, few arteries are available, and they are small. If one of the few small arteries that are available is harvested for endothelial culture, that artery is no longer available for any future cardiac bypass procedures.

In some cases, human arterial endothelial cells used with the polymeric vascular grafts of this disclosure are modified such that they can serve as universal donor cells. In some cases, the cells are genetically modified. By the term "modified" as used herein, is meant a changed state or structure of a molecule or cell of this disclosure. Molecules may be modified in many ways, including chemically, structurally, and functionally. Cells may be modified through the introduction of nucleic acids. In certain embodiments, a modified cell may be "genetically modified" or "genetically edited", wherein one or more nucleic acids in the cell are altered. The terms "genetically engineered", "genetically edited", and "genetically modified" are used interchangeably herein and refer to a cell (e.g., prokaryotic or eukaryotic cell) wherein one or more nucleic acids in the cell are altered or a cell that has been modified to comprise a non-naturally occurring nucleic acid molecule that has been created or modified by the hand of man (e.g., using recombinant DNA technology) or is derived from such a molecule (e.g., by transcription, translation, etc.).

An arterial endothelial cell that contains an exogenous, recombinant, synthetic, and/or otherwise modified polynucleotide is considered to be a genetically modified cell and, thus, non-naturally occurring relative to any naturally occurring counterpart. In some cases, genetically modified cells contain one or more recombinant nucleic acids. In other cases, genetically modified cells contain one or more synthetic or genetically engineered nucleic acids (e.g., a nucleic acid containing at least one artificially created insertion, deletion, inversion, or substitution relative to the sequence found in its naturally occurring counterpart). Procedures for producing genetically engineered cells are generally known in the art, and are described in Sambrook et al, *Molecular Cloning, A Laboraory Manual*, Cold Spring Harbor Press, Cold Spring Harbor, N.Y. (1989), incorporated herein by reference.

In some cases, a cell's genome is modified (e.g., engineered) such that the modified cell "universally acceptable" for therapeutic applications. As used herein, the term "universally acceptable" refers general acceptance of cell products in immunological terms, where cross-matching of patients and cells is not required, and no immunosuppression is needed. In some cases, the cell is modified such that functional proteins encoded by either the class II or both the class I and the class II major histocompatibility complex genes do not appear on the cell's surface. In this way, the modified cells are more likely to evade attack by T-cells of the graft recipient. In some cases, human arterial endothelial cells are genetically modified (engineered) as described in U.S. Pat. No. 6,916,654. In other cases, it may be advantageous to produce immune non-responsive cells from iPS cells by disrupting beta-2 microglobulin as described by as U.S. Patent Pub. 2014/0134195. For example, a cell can be modified to comprise a genetically engineered disruption in the cell's endogenous beta-2 microglobulin (B2M) gene. As described in U.S. Patent Pub. 2014/0134195, the genetically engineered disruption can comprise introducing one or more polynucleotide sequences capable of encoding a single chain fusion human leukocyte antigen (HLA) class I protein comprising at least a portion of the B2M protein covalently linked, either directly or via a linker sequence, to at least a portion of a human leukocyte antigen (HLA)-I chain. It will be understood, however, that methods of obtaining "universal" human AECs are not limited to modifying HLA proteins. In some cases, AECs are derived from induced pluripotent stem cells that are at least 50% HLA matched to the patient to receive the vascular graft.

Other strategies can also be used to genetically modify cells to minimize the immune response. For example, Riolobos et al. (*Molecular Therapy* 2013, 21(6):1232-1241) described producing stable HLA-I negative human pluripotent cells by making targeted disruptions in both alleles of the Beta-2 Microglobulin (B2M) gene using recombinant adeno-associated virus (rAAV)-mediated gene editing. The resulting $B2M^{-/-}$ pluripotent stem cells could be differentiated into human AECs according to the chemically defined methods of U.S. Patent Pub. 2016/0244719 to produce non-immunogenic "universal" human AECs for use with polymeric vascular grafts of this disclosure. In another example, genetic modifications that wholly or partially disrupt expression of CD58 on the cell surface have been shown to increase escape from immune recognition by both arms of cellular immunity. See, e.g., Challa-Malladi et al. (*Cancer Cell* 2011; 20(6):728-740). Also, HLA-E-expressing pluripotent stem cells (Edimer cells) evade allogeneic responses and lysis by NK cells (Gornalusse et al., *Nat Biotechnol.* 2017; 35(8):765-772).

In some cases, cells for the vascular grafts provided herein are modified without the introduction of a transgene into the genome of a cell. In some cases, for example, AECs are gene edited to modulate expression of an endogenous gene (e.g., increase expression or decrease expression relative to a control, unmodified cell). Any suitable means of gene editing can be used. Various gene editing technologies are known to those skilled in the art. Gene editing technologies include, without limitation, homing endonucleases, zinc-finger nucleases (ZFNs), transcription activator-like effector (TALE) nucleases (TALENs), clustered regularly interspaced short palindromic repeats (CRISPR)-CRISPR-associated protein (e.g., Cas9) genome editing systems, and CRISPR-Cpfl genome editing systems. Homing endonucleases generally cleave their DNA substrates as dimers, and do not have distinct binding and cleavage domains. ZFNs recognize target sites that consist of two zinc-finger binding sites that flank a 5- to 7-base pair (bp) spacer sequence recognized by the FokI cleavage domain. TALENs recognize target sites that consist of two TALE DNA-binding sites that flank a 12- to 20-bp spacer sequence recognized by the FokI cleavage domain. The Cas9 nuclease is targeted to DNA sequences complementary to the targeting sequence within the single guide RNA (gRNA) located immediately upstream of a compatible protospacer adjacent motif (PAM) that may exist on either strand of the DNA helix. Accordingly, one of skill in the art would be able to select the appropriate gene editing technology for the present invention.

In some cases, gene editing technology (e.g., a CRISPR-Cas9 gene editing system) can be used to modify human pluripotent stem cells in such a way that they are functionally "invisible" to the immune system. Such "universally acceptable" pluripotent stem cells can be differentiated into AECs for use in a vascular graft of this disclosure. In some cases, AECs are modified to induce overexpression of CD47 as means of evading detection by the innate immune system. CD47 is known as a key immune checkpoint which is highly expressed on tumor cells, making tumor cells resistant to host immune surveillance. In some cases, CD47 overexpression is induced by the introduction of a virus containing the CD47 gene, which delivers extra copies of the gene into the cells. See e.g., Deuse et al., *Nature Biotechnology* 37, 252-258 (2019). As used herein, the terms "overexpress" and "overexpression" refer to increasing the expression of a gene product (e.g., mRNA, protein) to a level greater than the cell normally produces. It is intended that the terms encompass overexpression of endogenous as well as exogenous proteins. In some cases, overexpression is determined relative to a reference standard.

In some cases, AECs are genetically modified to express a selectable marker. In such cases, expression of the selectable marker is used to identify and/or isolate modified cells from unmodified cells. In this manner, selectable marker expression is used to obtain pure or substantially pure populations of modified cells for use in a vascular graft of this disclosure. In some cases, AECs are modified to comprise a selectable marker cassette. The selectable marker cassette may confer resistance to drug such as an antibiotic. Those of skill in the art will appreciate that additional selectable markers or combinations of selectable markers can be used as well. Other forms of selectable markers may be used such as markers that provide a growth advantage or colorimetric selection other than antibiotic resistance. Preferably, selectable marker cassettes include a polynucleotide encoding the selectable marker operably connected to a promoter or regulatory region capable of inducing transcription of the selectable marker, more preferably, specifically in endothelial cells. Use of endothelial cell-specific promoters enable purification of endothelial or arterial endothelial cells from contaminating cells that do not express that gene. Promoters useful in the practice of the present invention include, but are not limited to, constitutive, inducible, temporally-regulated, and chemically regulated promoters. Preferably, the promoters are inducible.

Following modification, AECs can be applied to a prepared polymeric substrate to prepare an AEC-seeded vascular graft for immediate use, later use, or storage. As used herein, the term "prepared" refers to a polymeric substrate that has been treated in preparation for assembling an AEC-seeded vascular graft. "Prepared" encompasses a polymeric substrate that was previously coated (partially or fully) and/or de-gassed. In some cases, AECs can be stored, for example in liquid nitrogen tanks, until needed for the treatment of a particular patient. For short-term storage (e.g., about 6-12 months), AECs can be stored at −80° C. or lower (e.g., −80°, −90°, −100°, −110°, −120° C., −130° C., −140° C., −150° C., −160° C., −170° C., −180° C., −190° C., −196° C., or lower). In some cases, AECs are maintained at temperature above 0° C. including, without limitation, 4° C., room temperature (about 25° C.), and about 37° C., prior to seeding onto a prepared polymeric substrate. The ability to prepare polymeric vascular grafts comprising universal AECs in advance and store them until needed is an important advantage, particularly for treatment of patients with an urgent need. In such cases, AEC-seeded polymeric vascular grafts are suitable for transplanting onto or implanting into a subject, where the graft induces reduced or no graft rejection in the subject.

In some cases, AECs for the vascular grafts provided herein are obtained from cell banks. Generally, cell banks collect cell samples from multiple sources, catalog them according to at least one predetermined characteristic, and store the cells under conditions that keep cells viable. Accordingly, stored or "banked" cells having particular predetermined characteristics are available upon demand. Preferably, banked cells representing many ILA types from healthy individuals are stored in cell banks in order to provide haplotype matches for all potential recipients in a particular population. In some cases, banked cells useful for the vascular grafts and methods provided herein are induced pluripotent stem cells (iPSCs) derived from screened and HLA-typed donors. In other cases, the banked cells are AECs derived from HLA-typed iPSCs. For example, AECs can be obtained from the HLA-typed iPSC according to the methods described in U.S. Patent Pub. 2016/0244719. An individual's HLA type comprises a pair of co-expressed haplotypes, each consisting of an HLA-A, HLA-B, HLA-C, HLA-DQ, HLA-DP, and HLA-DR. In other cases, HLA-matched human embryonic stem cells (hESCs) are used. Depending on the ethnic make-up of a given population of individuals, the frequency of certain HILA allele combinations will vary. Using algorithms, it is possible to determine the frequency of each HLA allele combination within a pool of tissue donors and the number of homozygous and heterozygous HLA types needed within a cell bank in order to provide an HLA match for 100° % of potential recipients. For review, see, e.g., de Rham & Villard, J. *Immunology Res.* 2014. Preferably, banked cells are generated from healthy donors having blood group O in order to reduce the potential risk of alloimmune reactions mediated by anti-ABO agglutinin (Zimmermann et al., Stem Cells mml Development 2012; 21(13):2364-2373).

Preparations comprising AEC cells useful for clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of clinical manufacturing of a cell therapy product, such as in vitro populations of human arterial endothelial cells for vascular grafts as provided herein, GTPs govern donor consent, traceability, and infectious disease screening, whereas the GMP is relevant to the facility, processes, testing, and practices to produce a consistently safe and effective product for human use. See Lu et al., *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases, results are statistically significant; and ethical guidelines are followed.

In some cases, human arterial endothelial cells can be obtained according to the methods described in U.S. Patent Pub. 2016/0244719. AECs obtained according to such methods are characterized by high levels of expression of arterial endothelium markers such as EphrinB2, DLL4, Hey-2, jagged-1, and jagged-2. The AECs are also characterized by low leukocyte adhesion, higher NO production and oxygen consumption, response to shear stress, and capacity to form vascular networks in vitro and in vivo while maintaining expression of arterial markers in such networks. The methods comprise or consist essentially of culturing mesodermal cells in a serum-free, albumin-free, chemically defined culture medium that is substantially free of insulin and comprises a fibroblast growth factor (FGF), a vascular endothelial growth factor (VEGF), and at least one of a Notch agonist, a TGF-beta inhibitor, and an inhibitor of inositol monophosphatase, where culturing occurs for a length of time sufficient for the cultured mesoderm cells to differentiate into arterial endothelial cells. Amounts of FGF, VEGF, Notch agonist, TGF-beta inhibitor, and inhibitor of inositol monophosphatase useful to differentiate human mesodermal cells (including pluripotent stem cell-derived mesodermal cells) into AECs are described U.S. Patent Pub. 2016/0244719. In some embodiments, the cell culture medium used for AEC differentiation methods described herein comprises each of these components. In other cases, the culture medium is substantially free of one or more of these ingredients. Culturing can take place on any appropriate surface (e.g., in two-dimensional or three-dimensional culture).

AECs characteristically have the following expression profile: $CD31^{+}/CD144^{+}/CD41^{-}/CD4^{-}$. Preferably, AECs express one or more of the following arterial endothelial cell markers: Ephrin B2 (EFNB2), Neuropilin-1 (NRP-1)/CD304, Delta-like 4 (DLL4), and CD184 (cluster of differentiation 184). The Ephrin B2 (EFNB2) gene encodes an EFNB class Ephrin that binds to the EPHB4 and EPHA3 receptors. Neuropilin-1 (NRP1), which is also known as vascular endothelial cell growth factor 165 receptor (VEGF165R), is primarily expressed in arterial endothelial cells. DLL4 is a Notch ligand expressed in arterial endothelial cells (Shutter et al., *Genes & Dev.* 14:1313-18 (2000)). CD184 is also known as CXCR4 (C-X-C chemokine receptor type 4) or fusin. Any appropriate method can be used to detect expression of biological markers characteristic of cell types described herein. For example, the presence or absence of one or more biological markers can be detected using, for example, RNA sequencing (e.g., RNA-seq), immunohistochemistry, polymerase chain reaction, quantitative real time PCR (qRT-PCR), or other technique that detects or measures gene expression. RNA-seq is a high-throughput sequencing technology that provides a genome-wide assessment of the RNA content of an organism, tissue, or cell. Alternatively, or additionally, one may detect the presence or absence or measure the level of one or more biological markers of AECs using, for example, via fluorescent in situ hybidization; (FISH; see WO98/45479 published October, 1998), Southern blotting, Northern blotting, or polymerase chain reaction (PCR) techniques, such as qRT-PCR. Quantitative methods for evaluating expression of markers at the protein level in cell populations are also known in the art. For example, flow cytometry is used to determine the fraction of cells in a given cell population that express or do not express biological markers of interest.

Preferably, the AEC population comprises at least 80% arterial endothelial cells. In some cases, at least about 80% (e.g., at least 80%, 85%, 90%, 95%, 99°%, or more) of cells in the resulting cell population are arterial endothelial cells.

The mesodermal cells can express one or more mesodermal markers selected from the group consisting of Brachyury (1), EMOS, FOXA2, MIXL1, MSX1, and AMSX2. For the methods described herein, mesodermal cells are typically cultured in a culture medium that is free, substantially free, or essentially free of insulin, albumin, or any component derived from a non-human animal (i.e., free of xenogeneic material). As used herein, the term "substantially free" refers to cell culture conditions substantially devoid of a certain component or reagent. Substantially free of insulin means the medium contains less than 1% of original concentration of insulin, or less than $2\times10^{-5}$% of insulin by weight, and preferably contains less than $1\times10^{-5}$%, less than $0.5\times10^{-5}$%, less than $0.2\times10^{-5}$% or less than $0.1\times10^{-5}$% of insulin.

TGFβ receptor inhibitors appropriate for use in a method of the present invention include, without limitation, SB-431542, SB-525334, A83-01, LY2157299, LY210976, RepSox, SB-505124, D4476, GW788388, SD208, and EW-7197. Preferably, the inhibitor of TGF-beta signaling is SB-431542, a small molecule inhibitor of endogenous Activin and the type I receptor (TGFβ Receptor 1)(Inman et al., *Mol Pharmacol.* 62(1):65-74 (2002).

Notch is a single-pass cell-surface receptor that binds to a family of cell-surface ligands including the Delta-like and Jagged families. As used herein, the terms "Notch agonist" and "Notch activator" refer to molecules (e.g., biomolecules, small molecules, chemicals) that bind to Notch receptor and initiate or mediate signaling events associated with Notch activation. Resveratrol (3,4',5-trihydroxystilbene) belongs to a class of polyphenolic compounds called stilbenes and is an activator (agonist) of Notch signaling. Other Notch agonists appropriate for use according to methods for promoting arterial differentiation provided herein include valproic acid and suberoyl bishydroxamic acid. In addition, immobilized or multimerized soluble Notch ligands such as immobilized DLL4 and immobilized Jagged-1 peptide also can be used as Notch activators.

Inositol monophosphatase (IMPase) catalyzes the hydrolysis of myo-inositol monophosphates to myo-inositol, which is required in the phosphoinositide cell signaling pathway. In some cases, an inhibitor of IMPase is the biphosphonate L-690,330 ([1-(4-Hydroxyphenoxy)ethylidene]bisphosphonic acid). Lithium also inhibits IMPase to attenuate phosphoinositide signaling (Berridge el al., *Cell* 59:411-419 (1989)). Other inhibitors of the phosphoinositide signaling pathway include, without limitation, phosphoinositide 3-kinase (PI3K) inhibitor Ly294002, Pictilisib, HS-173, GSK2636771, Duvelisib, TG100-115, GSK1059615, PF-04691502, PIK-93, BGT226, AZD6482, SAR245409, BYL719, CUDC-907, IC-87114, TG100713, Gedatolisib, CH5132799, PKI-402, BAY 80-6946, XL147, PIK-90, PIK-293, PIK-294, Quercetin, Wortmannin, ZSTK474, AS-252424, AS-604850, and Apitolisib.

A suitable working concentration range for chemical inhibitors of IMPase, TGFβ receptors, and other described herein is from about 0.1 μM to about 100 μM, e.g., about 2 μM, 5 μM, 7 μM, 10 μM, 12 μM, 15 μM, 18 μM, or another working concentration of one or more the foregoing chemical inhibitors between about 0.1 μM to about 100 μM.

Preferably, mesodermal cells are cultured in the AEC differentiation medium until at least about 800% (e.g., at least 80%, 85%, 90%, 95%, 98%, or more) of cells in the resulting cell population are arterial endothelial cells.

For several of the biological markers described herein, expression will be low or intermediate in level. While it is commonplace to refer to cells as "positive" or "negative" for a particular marker, actual expression levels are a quantitative trait. The number of molecules on the cell surface can vary by several logs, yet still be characterized as "positive." Accordingly, characterization of the level of staining permits subtle distinctions between cell populations. Expression levels can be detected or monitored by flow cytometry, where lasers detect the quantitative levels of fluorochrome (which is proportional to the amount of cell surface antigen bound by the antibodies). Flow cytometry or fluorescence-activated cell sorting (FACS) can be used to separate cell populations based on the intensity of antibody staining, as well as other parameters such as cell size and light scatter. Although the absolute level of staining may differ with a particular fluorochrome and antibody preparation, the data can be normalized to a control.

In some cases, the arterial endothelial cells are derived from human pluripotent stem cells. As described in U.S. Patent Pub. 2016/0244719, human pluripotent stem cells are cultured for a period of about two days in a serum-free, albumin-free, chemically defined cell culture medium comprising a Bone Morphogenetic Protein (BMP), Activin A, and an activator of Wnt/β-catenin signaling, whereby a cell population comprising mesodermal cells is obtained. The mesodermal cells can express one or more mesodermal markers selected from the group consisting of Brachyurv (T), EMOS, FOXA2, MIXL1, MSX1, and MSX2.

Human pluripotent stem cells (hPSCs), either embryonic or induced, provide access to the earliest stages of human development and offer a platform on which to derive a large number of cells for cellular therapy and tissue engineering. Accordingly, in exemplary embodiments, the methods provided herein further comprise differentiating human pluripotent stem cells under conditions that promote differentiation of mesodermal stem cells into arterial endothelial cells. In some cases, the method of producing an arterial endothelial cell comprises culturing human pluripotent stem cells in a serum-free, albumin-free, chemically defined culture medium that promotes mesoderm differentiation. Pluripotent stem cell-derived mesodermal cells are then differentiated according to AEC differentiation methods (e.g., those described in U.S. Patent Pub. 2016/0244719), thus producing pluripotent stem cell-derived AECs In exemplary embodiments, the serum-free, albumin-free, chemically defined culture medium that promotes mesoderm differentiation comprises Activin A, Bone Morphogenetic Protein 4 (BMP4), FGF2, and an activator of Wnt/3-catenin signaling. The pluripotent stem cells can be human embryonic stem cells or human induced pluripotent stem cells. As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81 Pluripotent stem cells appear as compact colonies comprising cells having a high nucleus to cytoplasm ratio and prominent nucleolus. ESCs are commercially available from sources such as WiCell Research Institute (Madison, Wis.).

In some cases, the arterial endothelial cells are derived from human induced pluripotent stem cells. For example, for patients without an acute need, induced pluripotent stem cells can derived from the patient to produce patient-specific arterial endothelial cells. As used herein, the term "induced pluripotent stem cells" ("iPS cells") refers to a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain AECs having the genetic complement of a particular human subject. For example, it may be advantageous to obtain AECs that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227):277-80 (2009): Howden et al., *Proc. Natl. Acad. Sc. U.S.A.* 108(16):6537-42 (2011). Subject-specific somatic cells for reprogramming into iPS cells can be obtained or isolated from a target tissue of interest by biopsy or other tissue sampling methods. In some cases, subject-specific cells are manipulated or modified in vitro prior to use. For example, subject-specific cells can be expanded, differentiated, chemically treated, genetically modified, contacted to polypeptides, nucleic acids, or other factors, cryopreserved, or otherwise modified prior to reprogramming and then directed differentiation of the reprogrammed cells to produce subject-specific AECs.

An important difference between arterial endothelial cells produced from iPS cells from a specific individual and primary arterial endothelial cells isolated from that same individual is that the iPS cell-derived cells are infinitely scalable and are capable of exceeding the Hayflick limit (a certain number of cell divisions). As used herein, the term "Hayflick limit" refers to a finite number of population doublings in vitro before a cell can no longer proliferate and enters senescence (Hayflick L. *Exp Cell Res* 37:614-36, 1965). While the inherent self-renewal capacity of primary cultured arterial endothelial cells is limited, an almost inexhaustible supply of arterial endothelial cells can be obtained according to the methods provided herein from a single source (e.g., a somatic cell of an individual). Accordingly, in an embodiment of the invention, the AECs are capable of expansion within the tissue culture laboratory such that the numbers of cells obtained is sufficient to treat more than one patient and, in the preferred embodiment, are suitable for cell banking.

Defined medium and substrate conditions for culturing pluripotent stem cells, as used in the methods described herein, are well known in the art. Preferably, the media used herein are chemically defined, albumin-free, and xeno-free. In some cases, pluripotent stem cells to be differentiated according to the methods disclosed herein are cultured in a chemically defined, serum-free, albumin-free medium.

In some embodiments, the proportion of arterial endothelial cells in a population of cells is enriched using a cell separation, cell sorting, or other enrichment method, e.g., fluorescence activated cell sorting (FACS), enzyme-linked immunosorbent assay (ELISA), magnetic beads, magnetic activated cell sorting (MACS), laser-targeted ablation of non-endothelial cells, and combinations thereof. Preferably, FACS is used to identify and separate cells based on cell-surface antigen expression. In some cases, after obtaining a cell population comprising human AECs according to a method described herein, the human AEC population can be expanded in a culture medium appropriate for proliferating human AECs including, without limitation, Human Endothelial Serum-Free Medium (Life Technologies. Cat No 11111-044), EGM-2 (Lonza, Cat. No. CC-3162), and Endothelial Cell Culture Medium (BD Biosciences, Cat. No. 355054).

C. Additional Vascular Graft Components

Depending on particular use to which a polymeric vascular graft as described herein will be applied, it will be advantageous in some cases for the graft to further comprise one or more bioactive agents. As used herein, the term "bioactive agent" or "active agent" refers to therapeutic, prophylactic, and/or diagnostic agents and includes, without limitation, biologically, physiologically, or pharmacologically active substances that act locally or systemically in the human or animal body. Examples can include, without limitation, small-molecule drugs, peptides, proteins, antibodies, sugars, polysaccharides, nucleotides, oligonucleotides, aptamers, siRNA, nucleic acids, and combinations thereof. "Bioactive agent" includes a single agent or a plurality of bioactive agents including, for example, combinations of two or more bioactive agents.

Bioactive agents appropriate for use with a polymeric graft of this disclosure include, without limitation, pharmaceutical compositions, polypeptides (e.g., chemokines, cytokines), and/or additional therapeutic agents or drugs including, without limitation, anti-thrombogenic agents, anti-proliferative agents, agents that prevent, inhibit, or reduce restenosis or aneurysm formation, antineoplastic/anti-proliferative/anti-mitotic agents, vascular cell growth promoters, vascular cell growth inhibitors, and vasodilating agents. Cytokine and chemokines include, without limitation, interleukin (IL)1α, IL-1β, IL-2, IL-3, R-4, IL-5, IL-6, IL-7, IL-9, IL-10, IL-12(p40), IL-12(p70), IL-13, IL-15, IL-17, IP-10, eotaxin, interferon γ (IFNγ), granulocyte colony-stimulating factor (G-CSF), granulocyte/macrophage colony-stimulating factor (GM-CSF), macrophage inflammatory protein 1α (MIP-1α), RANTES, tumor necrosis factor-alpha (TNF-α), platelet-derived growth factor (PDGF)-AA, PDGF-AB/BB, TGF-beta, VEGF, and combinations thereof. In some cases, the bioactive agent is incorporated into a vascular graft or applied to a vascular graft.

In some cases, polymeric vascular grafts comprises one or more additional cell types. For example, smooth muscle cells (SMCs) can be seeded onto a polymeric vascular graft in addition to AECs. The SMCs can be primary smooth muscle cells or human pluripotent stem cell-derived SMCs. The SMCs can be wild-type, genetically modified, or gene edited.

Methods

The polymeric vascular grafts described herein are useful as arterial or arterial-venous shunts for any vascular or cardiovascular surgical application Exemplary applications include, without limitation, congenital heart surgery, coronary artery bypass surgery, and peripheral vascular surgery. Accordingly, in another aspect, provided herein are methods of producing and using the polymeric vascular grafts provided herein to treat a blood vessel defect in a subject in need thereof. Such a method may include implanting the polymeric vascular grafts disclosed herein in a subject in need thereof. The terms "individual," "host," "subject," and "patient" are used interchangeably herein. In various embodiments, the polymeric vascular grafts are implanted to replace of a portion of a diseased or damaged blood vessel, for example, to replace a weakened portioned of the aorta or vessels damaged due to trauma or damaged due to a vascular disease.

In some embodiments, a polymeric vascular graft is used to bypass and/or replace a stenotic or partially occluded segment of a blood vessel, for example, in coronary or peripheral artery bypass graft procedure. For example, AEC-seeded polymeric vascular grafts of this disclosure are useful for bypass operations in the heart or leg. In another example, AEC-seeded polymeric vascular grafts of this disclosure are useful in reconstructive surgeries, for example to correct developmental abnormalities or to repair severe injuries. The vascular grafts are also well suited to provide hemodialysis access in arterial-venous shunts.

In some cases, a method of treating comprises performing an anastomosis (i.e., the surgical union of tubular parts) to implant the polymeric vascular graft. Typically, an anastomosis between the in situ artery or vein and the polymeric vascular graft is created by sewing the graft to the in situ vessel with suture. Commonly used suture materials include PROLENE® polypropylene sutures and ePTFE. Accordingly, vascular grafts of this disclosure comprise a suturable material such as PTFE or ePTFE.

One of the major problems with existing autologous venous endothelial cell procedures is that it takes about a month to harvest, grow, seed, and culture the cells on the graft. About 30% of patients cannot undergo the procedure because their medical acute need does not permit waiting for 30 days to obtain an autologous venous endothelial cell graft. Accordingly, this disclosure provides materials and methods that are particularly advantageous over conventional methods. In particular, provided herein are methods in which AEC-seeded polymeric vascular grafts are prepared and ready for clinical use within about 10 days. Such grafts are prepared using human AECs produced at scale and frozen until needed. In some cases, therefore, the method comprises thawing human AECs, seeding onto a polymeric substrate, preferably a polymeric substrate that has been at least partially coated with one or more endothelial cell adhesion agents. Upon request, frozen human AECs are selected based on a match to the patient in need of the graft or are "universal" AECs that are not likely to be immunogenic to the graft recipient (the patient). Preferably, the selected cells are thawed and seeded onto a prepared polymeric substrate, and the AEC-seeded polymeric substrate is cultured for fewer than 10 days, and preferably fewer than 7 days (e.g., as few as 2, 3, 4, 5, or 6 days). The cultured polymeric substrate is then delivered to or provided for therapeutic use with the patient within about 10 days, and preferably within about 7 days from the initial request. In cases in which AECs are derived from banked iPSC cells according to, for example, AEC differentiation protocols described in U.S. Patent Pub. 2016/0244719, the time from initial request to delivery of a prepared AEC-seeded vascular graft must encompass time to complete the differentiation process. This application provides directed differentiation protocols in which, in some cases, human pluripotent stem cells are differentiated into mesodermal cells in about 2-3 days, and the resulting mesodermal cells are induced to differentiate into endothelial cells in approximately 3 days. In some cases, the method comprises seeding a polymeric vascular graft with cells of a universal cell line. In such cases, seeded vascular grafts can be prepared and ready as an "off-the-shelf" product upon demand. In this case, AEC seeded vascular grafts can provided to a patient in need thereof as soon as they are required. For example, a prepared "universal" AEC-seeded vascular graft can be provided using overnight or faster delivery. If produced locally, delivery of a prepared vascular graft may require only a matter of minutes or hours. In some cases, prepared "universal" AEC-seeded vascular grafts can be purchased and locally stored as cryopreserved, frozen products, in which case AEC-seeded grafts can be available for patient use with minimal delay.

Any appropriate method can be used to detect and measure functional and morphological changes following implantation of a polymeric vascular graft of this disclosure. For example, vascular ultrasonography can be performed to evaluate fluid flow in the arteries and veins of the body to detect the presence, severity, and/or specific location of disease. Vascular ultrasonography is a noninvasive ultrasound method (also called duplex ultrasonography) used to examine circulation in the blood vessels of the body. In some cases, vascular ultrasonography is used to calculate speed of fluid flow in a blood vessel before and after treatment of the vessel with a polymeric vascular graft as described herein. In some cases, contrast-enhanced ultrasonography (CEUS) is used to detect and/or monitor vascular pathologies before and after interventions. Vascular ultrasonography and CEUS are particularly useful to detect and characterize post-intervention restenosis. "Restenosis," as defined herein, means a narrowing of the lumen of a blood vessel at a previously stenotic site (i.e., the site of balloon inflation during angioplasty), or narrowing of the lumen of a blood vessel or synthetic graft following an interventional procedure (e.g., narrowing of the venous side of an arterial-venous anastomosis following bypass surgery using a graft). Restenosis, as used herein, encompasses occlusion. Restenosis includes any luminal narrowing that occurs following an injury to the vessel wall. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis.

In another aspect, provided herein is a method of fabricating a polymeric vascular graft. The method can comprise or consist essentially of coating at least a portion of a polymeric substrate with one or more endothelial attachment agents; and contacting human arterial endothelial cells to the coated polymeric substrate, thereby forming an AEC-seeded polymeric vascular graft which is substantially non-adhesive to leukocytes or cellular fragments thereof. As used herein, the term "coating" refers to attaching or depositing, by any suitable process, an endothelial attachment agents of this disclosure onto a polymeric material (e.g., ePTFE) such that the deposited agent covers across some or all surfaces of the material. In some cases, coating comprises covering, at least partially, inner lumen surface areas of the polymeric material. Coating of a polymeric material does not have to be complete. In particular, it is preferable in some cases to provide composition to only a portion or some portions of the polymeric material to be coated, thus resulting in a polymeric material that is at least partially coated by one or more endothelial attachment agents. In some cases, a coating includes one or more coating layers. A coating can have a substantially constant or a varied thickness.

In some cases, coating at least a portion of the polymeric substrate is performed at room temperature or at a temperature that is physiologically relevant to arterial endothelial cells such as 37° C. In some cases, coating comprises contacting at least a portion of the polymeric substrate with one or more endothelial attachment agents for any appropriate length of time including, without limitation, a few minutes, a few hours, or about 12 hours to about 24 hours, whereby a partially or fully coated substrate is obtained.

In some cases, the method optionally comprises degassing the polymeric substrate prior to coating with one or more endothelial cell attachment agents.

In another aspect, provided herein is a method of cryopreserving a AEC-seeded polymeric vascular graft. Cryopreservation is a process wherein biological materials such as cells, tissues, extracellular matrix, organs, or any other biological constructs susceptible to damage caused by unregulated chemical kinetics are preserved by cooling to very low temperatures (typically ~40° C. or −80° C.). The method can comprise or consist essentially of contacting a AEC-seeded polymeric vascular graft to a cryoprotectant (also referred to as cryoprotective agents, cryoprotectant agents, and cryopreservatives) and then exposing the contacted material to freezing temperatures. The cryoprotectant protects biological material on the vascular graft from the damaging effects of freezing (such as ice crystal formation and increased solute concentration as the water molecules in the biological material freeze). In some cases, the cryopreserved vascular graft retains at least 40%, 45%, 50%, 55%, 60%, 65%, 70%, 75%, 80%, 85%, 90% or 95% AEC cell viability after freezing and thawing as determined by the cell count on the graft tissue before processing and cell count in the graft after freezing and thawing.

In another aspect, provided herein is a method for delivering an arterial endothelial cell-seeded vascular graft, the method comprising: upon receipt of a request for an arterial endothelial cell-seeded vascular graft, selecting human arterial endothelial cells; seeding the selected human AECs onto a polymeric substrate at least partially coated by an endothelial cell attachment agent; culturing the seeded polymeric substrate for about 2 to about 10 days, whereby an AEC-seeded polymeric substrate suitable for implantation as a vascular graft is produced; and delivering the AEC-seeded vascular graft within about 10 days from receipt of the request. The polymeric substrate can be selected from expanded polytetrafluoroethylene (ePTFE), poly vinyl chloride (PVC), PGA (poly glycolic acid), PLA (poly lactic acid), PCL (poly caprolactone), PGLA (polylactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracelluar matrix protein-based scaffold, hyaluronic acid, chitosan, and polyhydroxyalkanoate. The endothelial cell attachment agent can comprise one or more of dopamine, fibrin glue, RGD peptides, vitronectin, and laminin.

In some cases, the vascular graft exhibits reduced leukocyte adhesion relative to a polymeric substrate seeded with venous endothelial cells. In some cases, the vascular graft exhibits reduced thrombosis relative to a polymeric substrate seeded with venous endothelial cells or a naked, uncoated polymeric substrate. In some cases, the vascular graft exhibits increased long-term patency rates relative to a polymeric substrate not coated with the endothelial cell attachment agent. In some cases, the method further comprises degassing the polymeric substrate prior to coating with the endothelial cell attachment agent. In some cases, de-gassing comprises washing the polymeric substrate in acetone and ethanol, washing the polymeric substrate in an organic solvent, or applying a vacuum. Preferably, the human arterial endothelial cells are non-immunogenic to a recipient of the vascular graft. In some cases, the human arterial endothelial cells comprise one or more genetic modifications such that they do not express a beta2-microglobulin gene. In some cases, the human arterial endothelial cells comprise one or more genetic modifications such that they do not express one or more proteins encoded by class I major histocompatibility complex (MHC) genes. In some cases, the human arterial endothelial cells comprise one or more genetic modifications such that they do not express one or more proteins encoded by class II major histocompatibility complex (MHC) genes. In some cases, the human arterial endothelial cells comprise one or more genetic modifications such that they do not express CD58 polypeptide. In some cases, the human arterial endothelial cells comprise one or more genetic modifications such that they over-express one or both of HLA-E (Edimer) and CD47.

In another aspect, provided herein is a method for delivering an arterial endothelial cell-seeded vascular graft, the method comprising: upon receipt of a request for an arterial endothelial cell-seeded vascular graft, selecting a cryopreserved arterial endothelial cell (AEC)-seeded vascular graft suitable for a subject in need thereof; thawing the selected cryopreserved AEC-seeded vascular graft; removing cryopreservation solution from the thawed AEC-seeded vascular graft, if present; and delivering the AEC-seeded vascular graft within about 1-2 days (e.g., within about 24 to about 48 hours) from receipt of the request. Importantly, these methods provide a solution to a critical need for patient care, specifically the ability to provide a patient-ready AEC-seeded vascular graft within one to two days (e.g., within about 24 to about 48 hours) of receipt of a request for the graft material. These methods thus provide a significant improvement over conventional methods, which require about 30 days to provide a vascular graft seeded with the patient's autologous venous endothelial cells. As used herein, the term "patient-ready" means that the graft is pre-configured and is ready for use with a patient with minimal delay or additional preparation.

In some cases, a suitable cryopreserved AEC-seeded vascular graft comprises human arterial endothelial cells that are non-immunogenic to the subject. The human arterial endothelial cells can comprise one or more genetic modifications such that they do not express one or more proteins encoded by class II major histocompatibility complex (MHC) genes. In some cases, the human arterial endothelial cells comprise one or more genetic modifications such that they do not express CD58 polypeptide. In some cases, the human arterial endothelial cells comprise one or more genetic modifications such that they over-express one or both of HLA-E (Edimer) and CD47.

Articles of Manufacture

In another aspect, provided herein are articles of manufacture. For example, provided herein is a container comprising a cryopreserved combination product and a cryopreservation solution, wherein the cryopreserved combination product comprises a human arterial endothelial cell population seeded onto an implantable polymeric substrate at least partially coated by an endothelial cell attachment agent. In some cases, the endothelial cell attachment agent comprises dopamine. As described herein, the human arterial endothelial cells are preferably non-immunogenic such that the polymeric graft is "universal" and suitable for use in any human subject in need thereof. For example, the human arterial endothelial cells can comprise one or more genetic modifications such that they do not express a beta2-microglobulin gene and/or one or more proteins encoded by class I or class II major histocompatibility complex (MHC) genes. The container can be a vial, cryotube, bag, or any other vessel suitable to contain a polymeric vascular graft and a cryopreservation solution. Preferably, the container can be stored at freezing temperatures including, without limitation, a temperature from 1° C. to about −196° C. or lower (e.g., 1°, 0°, −1°, −5, −10°, −20°, −30°, −40°, −50°, −60°, −70°, −80°, −90°, −100°, −110°, −120°, −130°, −140°, −150°, −160°, −170°, −180°, −190°, −196° C., or lower).

In some cases, the human arterial endothelial cell population is contacted with a cryopreservation solution prior to seeding onto the implantable polymeric substrate. In other cases, the implantable polymeric substrate is contacted to a cryopreservation solution after seeding by human arterial endothelial cells. Examples of suitable cryopreservation solutions include, without limitation, dimethyl sulfoxide (DMSO). In some cases, a 10% DMSO solution is used for cryopreservation. In some cases, the cryopreservation solution is removed from the seeded implantable polymeric substrate prior to implantation. The solution contacting and removal steps are generally carried out under aseptic, preferably sterile, conditions.

In another aspect, provided herein is a container comprising a cryopreserved combination product and a cryopreservation solution, wherein the cryopreserved combination product comprises a human arterial endothelial cell-seeded implantable polymeric substrate, wherein the implantable polymeric substrate is at least partially coated by one or more endothelial cell attachment agents. The polymeric substrate can be selected from expanded polytetrafluoroethylene (ePTFE), poly vinyl chloride (PVC), PGA (poly glycolic acid), PLA (poly lactic acid), PCL (poly caprolactone), PGLA (polylactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracelluar matrix protein-based scaffold, hyaluronic acid, chitosan, and polyhydroxyalkanoate. In some cases, the human arterial endothelial cells are non-immunogenic to a recipient of the implantable polymeric substrate. In some cases, the human arterial endothelial cells comprise one or more genetic modifications such that they do not express a beta2-microglobulin gene. The human arterial endothelial cells can comprise one or more genetic modifications such that they do not express one or more proteins encoded by class I and/or class II major histocompatibility complex (MHC) genes. In other cases, the human arterial endothelial cells comprise one or more genetic modifications such that they do not express CD58 polypeptide. Alternatively or additionally, the human arterial endothelial cells can comprise one or more genetic modifications such that they over-express one or both of HLA-E (Edimer) and CD47. The container can be a vial, cryotube, or bag. The cryopreservation solution can comprise about 10% dimethyl sulfoxide (DMSO). In some cases, the human arterial endothelial cell population is contacted with cryopreservation solution prior to seeding onto the implantable polymeric substrate. Preferably, the cryopreservation solution is removed from the seeded implantable polymeric substrate prior to implantation. Preferably, the combination product is configured for storage at a temperature from 37° C. to about −196° C. (e.g., about 37°, 30°, 25°, 15°, 10°, 4°, 1°, 0°−1°, −5, −10°−20°, −30°, −40°, −50°, −60°, −70°, −80°, −90°, −100°, −110°, −120°, −130°, −140°, −150°, −160°, −170°, −180°, −190°, −196° C., or lower) without a significant loss of cell viability relative to a control not stored under such conditions.

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application are specifically and individually indicated to be incorporated by reference, unless only specific sections of patents or patent publications are indicated to be incorporated by reference.

In order to further clarify this disclosure, the following terms, abbreviations and definitions are provided.

The indefinite articles "a" and "an," as used herein in the specification and in the claims, unless clearly indicated to the contrary, should be understood to mean "at least one." Any reference to "or" herein is intended to encompass "and/or" unless otherwise stated.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The terms "comprising", "comprises" and "comprised of as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. In other words, the terms are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

The following examples are provided to better explain the various embodiments and should not be interpreted in any way to limit the scope of the present disclosure.

EXAMPLES

Improvement of the cell adhesion by surface Modification of ePTFE

Meinhart et al. (ASAIO J 43:M515-521, 1997) reported the construction of venous endothelialized ePTFE (expanded polytetrafluoroethylene) vascular grafts that exhibit improved in vivo patency relative to ePTFE without venous endothelial cells. Since arterial grafts are preferable to venous grafts for artery bypass surgery, we seeded arterial endothelial cells on ePTFE to further improve patency. ePTFE is hydrophobic and thus demonstrates low cell adhesion. In order to improve cell adhesion, we performed plasma treatment to make ePTFE hydrophilic. The results demonstrated that plasma treatment enhanced the cell density but it's only about 20% confluence (FIG. 1A), which suggesting that cell adhesion molecular is required to further improve cell attachment. Since RGD peptides, collagen, fibronectin (FN), laminin, vitronectin (VTN), and Matrigel® are widely used for cell adhesion, we coated ePTFE with these cell attachment agents. The cells were then seeded on ePTFE by using a cell-seeding device. After seeding, the cells were further cultured for 2-20 days in culture medium comprising basal medium supplemented with FGF, VEGF, TGF-beta inhibitor (e.g., SB431542), and Resveratrol (RESV) to form chemically defined FVIR medium (see Table 1). Surprisingly, only Matrigel® and VTN were able to achieve greater than 95% cell confluence (FIG. 1B).

Next, we coated ePTFE with dopamine (FIG. 2A), which was able to undergo self-polymerization and deposition to the surface of ePTFE. The results demonstrated that dopamine coating improved cell density and reduced cell death on synthetic substrates (FIGS. 2B-2C). Fibrin glue was used for improving endothelial cell seeding on ePTFE (Zilla et al., 1989). However, this method includes multiple steps and thus is challenging to scale up for large-scale clinical applications. Thus, we investigated whether other endothelial cell adhesion agents such as dopamine can be used in place of fibrin glue for cell seeding. We compared cell seeding on ePTFE that was coated with dopamine. As shown in FIG. 2D, immunostaining revealed that AEC density was comparable on dopamine- and fibrin glue-coated ePTFE. These data demonstrate that various endothelial cell adhesion agents can be used for seeding polymeric substrates with human AECs.

TABLE 1

| Chemically defined FVIR medium formulation medium components |
|---|
| DMEM/F12 |
| L-ascorbic acid-2-phosphate magnesium (64 ng/mL) |
| Sodium selenium (14 ng/mL) |
| $NaHCO_3$ (543 μg/mL) |
| Transferrin (10.7 μg/mL) |
| Insulin (20 μg/mL) |
| FGF2 (100 ng/mL) |

TABLE 1-continued

| Chemically defined FVIR medium formulation medium components |
|---|
| $VEGFA_{165}$ (50 ng/mL) |
| TGF-β inhibitor SB431542 (10 μM) |
| RESV (5 μM) |

Comparison of Cell Seeding Efficiency of Dopamine- and Fibrin Glue-Coated ePTFE

Fibrin glue was used for improving endothelial cell seeding on ePTFE (Zilla et al., 1989). However, this method includes multiple steps and thus is challenging to scale up for large-scale clinical applications. Thus, we investigated whether other endothelial cell adhesion agents such as dopamine and extracellular matrix peptides and proteins can be used in place of fibrin glue for cell seeding. We compared cell seeding on ePTFE that was coated with dopamine, fibrin glue, RGD (Arg-Gly-Asp) peptides, VTN (vitronectin), and laminin. As shown in FIG. 2A, immunostaining revealed that AEC density was comparable on dopamine- and fibrin glue-coated ePTFE. As shown in FIG. 2B, AECs adhered well to ePTFE coated with RGD peptides, vitronectin, and laminin. These data demonstrate that various endothelial cell adhesion agents can be used for seeding polymeric substrates with human AECs.

AEC-ePTE Demonstrates Lower Leukocyte Adhesion

Increased leukocyte adhesion is a hallmark of initiation of atherosclerosis (De Caterina et al., 1995: Legein et al., 2013). Arterial endothelial cells (AECs) demonstrated lower leukocyte adhesion when compared to venous endothelial cells in static culture (Zhang et al., 2017), suggesting that AECs are more resistant to atherosclerosis. To investigate whether ePTFE material seeded with human AECs ("AEC-ePTFE grafts") maintain arterial specific function with flow, we compared leukocyte adhesion on ePTFE seeded with AECs and HUVEC (human umbilical venous endothelial cells; "HUVEC-ePTFE grafts"), respectively. Leukocytes were stained by exposure to 2 μM calcein AM for about 15 minutes. The calcein AM-labeled leukocytes were then added to AEC- and HUVEC-seeded ePTFE at a cell density of about $1\times10^6$ cells/ml. Both the calcein AM-labeled leukocyte cell suspension and ePTFE were placed into a 0.5 ml tube, and the tube was rotated at 60 rpm for 1 hour. One hour later, the cell-seeded ePTFE was gently washed with fresh media 3 times and then fixed and stained with DAPI for imaging. To mimic fluid flow through a vessel, leukocyte adhesion assays were performed under shear stress.

Figures 3A, 3B:
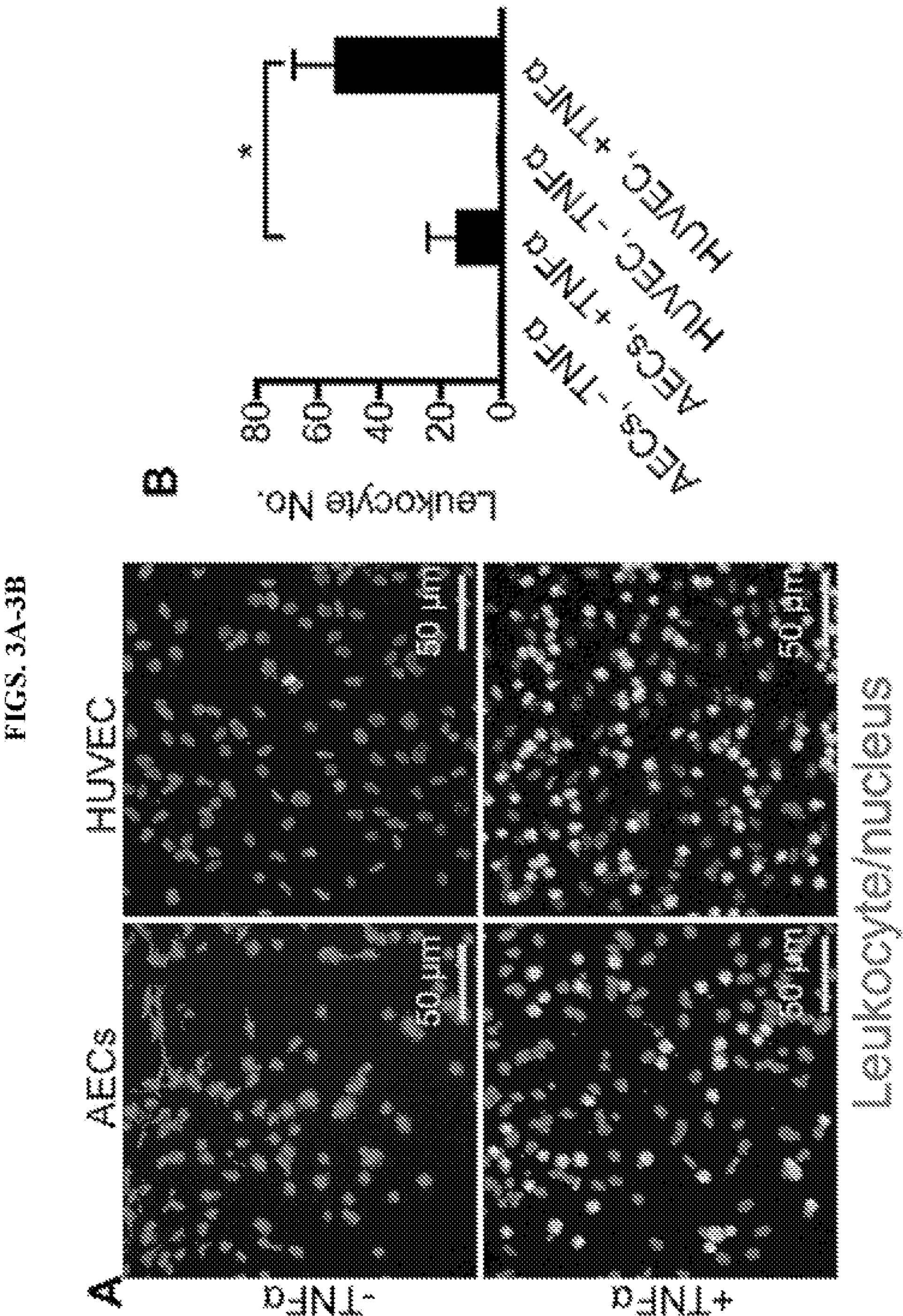
FIGS. 3A-3B demonstrate the results of leukocyte adhesion assays. (A) AECs and human umbilical vein endothelial cells (HUVECs) were seeded on dopamine-coated ePTFE. The seeded ePTFE substrates were cultured for three days, and then treated with 10 ng/ml TNFα or control for 4-5 hours. Leukocytes were stained by exposure to 2 μM calcein AM for about 15 minutes. The calcein AM-labeled leukocytes were then added to AEC- and HUVEC-seeded ePTFE at a cell density of about $1\times10^6$ cells/mi. Both the calcein AM-labeled leukocyte cell suspension and ePTFE were placed into a 0.5 ml tube, and the tube was rotated at 60 rpm for 1 hour. One hour later, the cell-seeded ePTFE was gently washed with fresh media 3 times and then fixed and stained with DAPI for imaging. (B) Statistics of leukocyte adhesion assay. Leukocytes were detected by immunostaining and counted for each image. Data are represented as mean±SD. *: P<0.05, n=3.

Before TNFα treatment, we observed few leukocytes attached to AEC-seeded and HUVEC-seeded substrates (FIG. 3A). Following TNFα treatment, many leukocytes were attached to HUVEC-ePTFE grafts, but far fewer leukocytes were attached to AEC-ePTFE grafts (FIGS. 3A-3B). The results suggested that AECs-ePTFE might be more resistant to vascular disease compared to venous endothelialized-ePTFE.

Figures 4A, 4B, 4C:
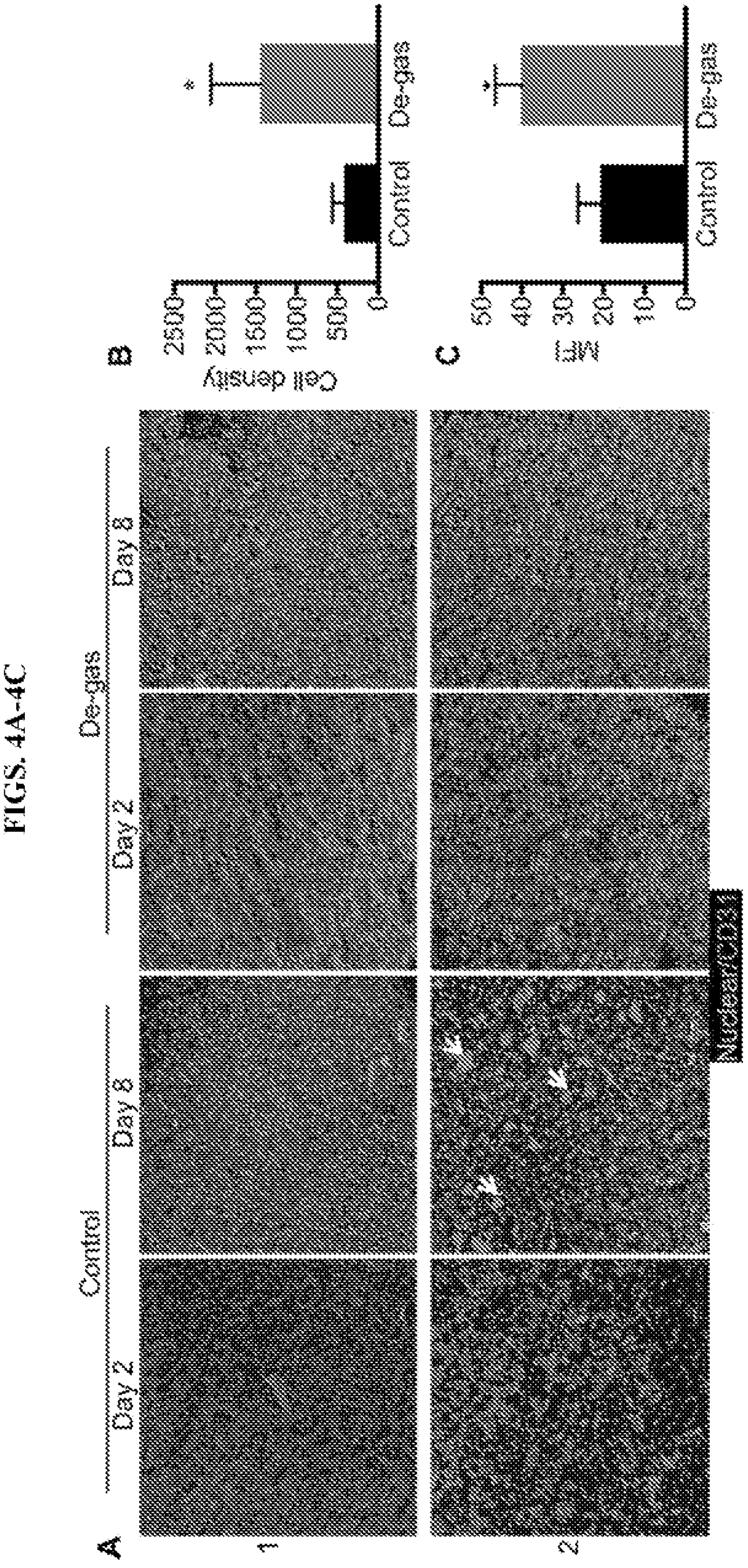
FIGS. 4A-4C demonstrate that de-gassing of ePTFE prevents cell aggregate formation and improves CD31 expression and cell density. (A) Arterial endothelial cells were seeded on the ePTFE with or without de-gas treatment. Two types of ePTFE, namely, 1 and 2, were used. Samples were collected for immunostaining 2- and 8-days after cell seeding. Arrows indicate cell aggregates, which were undetectable after de-gas treatment. (B) Statistics of cell density. Cell density on seeded substrates was determined by comparing the number of nuclei before and after de-gas at day 8. Data are represented as mean *SD. *: P<0.05, n=4. (C) Statistics of relative mean fluorescence intensity (MFI) of CD31. Data are represented as mean±SD. *: P<0.05, n=4.

De-Gas of ePTFE Prevents Cell Aggregate Formation and Improves CD31 Expression and Cell Density ePTFE vascular grafts comprise 70% of air by volume (Bensen et al., 1991). Upon fluid flow, bubbles or gas nuclei will be generated on the surface of ePTFE (Bensen et al., 1991), which may compromise the dopamine coating and, thus, endothelialization. We performed de-gas by using acetone and ethanol. ePTFE was submerged into acetone for 10-60 minutes, and then subjected to 30-minute rinses in each of 100% EtOH, 90% EtOH, and 70% EtOH. The de-gassed ePTFE was kept in $H_2O$ until use. After de-gas, the ePTFE was coated by dopamine and then seeded with AECs. It was observed that the mean fluorescent intensity of CD31 expression (red staining) increased after de-gas (FIGS. 4A, 4C). De-gas also increased cell density on seeded substrates as determined by comparing the number of nuclei before and after de-gas at day 8 (FIGS. 4A, 4B). In addition, CD31 expression was also increased, as measured by the fluorescence intensity of CD31 (FIGS. 4A, 4C). It was observed that cell aggregates formed on AEC-seeded ePTFE sample 2 (FIG. 4A), but de-gas treatment reduced the number of cell aggregates (FIG. 4A). Together, these data demonstrated that de-gas improved endothelialization of ePTFE.

Figures 5A, 5B, 5C:
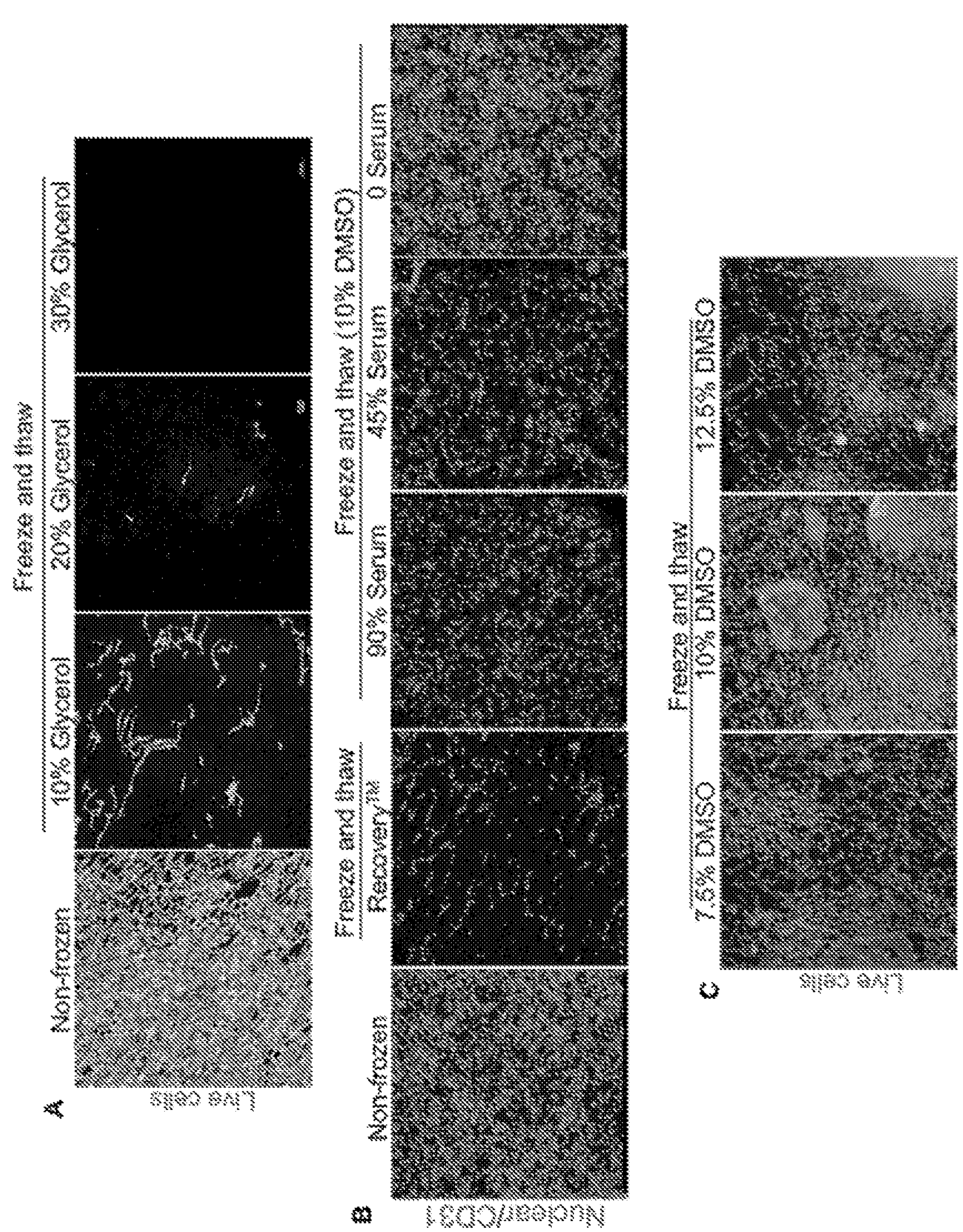
FIGS. 5A-5C demonstrate analysis of freezing media. (A) Glycerol is not suitable for freezing AEC-ePTFE. (B) Comparing Recovery™ Cell Culture Freezing Medium (Thermofisher), 10% DMSO, and serum for freezing AEC-ePTFE. (C) Optimization of DMSO concentration. Serum-free and Xeno-free media is used for freezing AEC-ePTFE, which was made by E5 media supplemented with 100 ng/mL FGF2, 50 ng/mL VEGFA, 10 μM SB431542, 5 μM RESV, and 20 μg/ml insulin).

To develop an "off the shelf" product, we tested various cryopreservation solutions for use with AEC-ePTFE vascular grafts. Glycerol was used for cryopreserve clinical used human skin substitute (US20140271583A1). However, our results demonstrated that glycerol was not suitable for cryopreservation of AEC-ePTFE vascular grafts (FIG. 5A). Recovery™ Cell Culture Freezing Medium (Thermofisher) improved cell viability in the cryopreservation of five different adherent and suspension cell lines, but most of the cells died when Recovery™ was used to freeze AEC-ePTFE vascular grafts (FIG. 5B). DMSO combined with FBS (fetal bovine serum) has been widely used for cryopreservation, generally (Ha et al., 2005). Interestingly, our results demonstrated that FBS reduced cell survival on frozen AEC-ePTFE grafts (FIG. 5B). In contrast, serum-free medium containing 10% DMSO showed the highest cell survival rate, which was comparable to cell survival in non-frozen control samples (FIG. 5B). Decreasing or increasing the DMSO concentration negatively impacted cell survival (FIG. 5C), indicating that 10% DMSO is well suited for cryopreservation of AEC-ePTFE vascular grafts.

Methods and Materials

Fibrin glue coaling: Fibrinogen component (Baxter, TISSEEL) was prepared by diluting a 2 ml portion of Fibrinogen with 4 ml heated Fibrinolysis inhibitor, and then adding 1 ml Tranexamic acid (20 mg/ml). Thrombin component was prepared by diluting 2 ml Fibrinogen in 4 ml $CaCl_2$), 75 ml $H_2O$, and 4 ml Tranexamic acid (20 mg/ml). Fibrinogen component was flowed through the ePTFE three times. Next, thrombin component was flowed through the ePTFE for 5 minutes. The ePTFE was rinsed with distilled water 3 times. After the coating steps were repeated once, ePTFE was flushed with 5 ml 50 U/ml heparin.

Dopamine coaling: Dopamine was dissolved into 10 mM Tris solution (pH=8.5) at 2 mg/mL concentration. ePTFE was immersed into the solution immediately and incubated in the solution at room temperature or 37° C. for 4-24 hours. Coated ePTFE was washed five times with distilled water.

Seeding cells on ePTFE: Endothelial cells were suspended at a density of ($1.5\times10^6$ cells/ml) in cell culture medium comprising Y27632 (a ROCK inhibitor) and seeded onto the ePTFE. The ePTFE was put into a tube and then loaded into a cell-seeding device (Endostradilisator III, Biggler). The ePTFE (in the tube) was rotated for 3 hours at 4 rph. Alternatively, the ePTFE can be incubated for 1 hour, then manually turned 90° and incubated for another hour. The 90° rotation was repeated for 4 times.

De-gas of ePTFE: De-gassing was performed by immersing ePTFE in acetone for 3 hours and then washing the acetone-treated ePTFE with 70% Ethanol for 30 minutes (repeated 3 times). The de-gassed ePTFE was rinsed in distilled water for 30 minutes (repeated 3 times). From this time point, ePTFE needs to be immersed in distilled water or phosphate buffered saline (PBS) to avoid re-gas.

REFERENCES

Bensen, C. V., Vann, R. D., Koger, K. E., and Klitzman, B. (1991). Quantification of gas denucleation and thrombogenicity of vascular grafts. *Journal of biomedical materials research* 25, 373-386.

De Caterina, R., Libby, P., Peng, H. B., Thannickal, V. J., Rajavashisth, T. B., Gimbrone, M. A., Jr., Shin, W. S., and Liao, J. K. (1995). Nitric oxide decreases cytokine-induced endothelial activation. Nitric oxide selectively reduces endothelial expression of adhesion molecules and proinflammatory cytokines. *J Cin Invest* 96, 60-68.

Deutsch, M., Meinhart, J., Fischlein, T., Preiss, P., and Zilla, P. (1999). Clinical autologous in vitro endothelialization of infrainguinal ePTFE grafts in 100 patients: a 9-year experience. *Surgery* 126, 847-855.

Deutsch, M., Meinhart, J., Zilla, P., Howanietz, N., Gorlitzer, M., Froeschl, A., Stuempflen, A., Bezuidenhout, D., and Grabenwoeger, M. (2009). Long-term experience in autologous in vitro endothelialization of infrainguinal ePTFE grafts. *Journal of vascular surgery* 49, 352-362.

Legein, B., Temmerman, L., Biessen, E. A., and Lutgens, E. (2013). Inflammation and immune system interactions in atherosclerosis. *Cell Mol Life Sci* 70, 3847-3869.

Meinhart, J., Deutsch, M., and Zilla, P. (1997). Eight years of clinical endothelial cell transplantation. Closing the gap between prosthetic grafts and vein grafts. ASAIO J43, M515-521.

Zhang, J., Chu, L. F., Hou, Z., Schwartz, M. P., Hacker, T., Vickerman, V., Swanson, S., Leng, N., Nguyen, B. K., Elwell, A., et al. (2017). Functional characterization of human pluripotent stem cell-derived arterial endothelial cells. *Proceedings of the National Academy of Sciences of the United States of America* 114, E6072-e6078.

Zilla, P., Fasol, R., Preiss, P., Kadletz, M., Deutsch, M., Schima, H., Tsangaris, S., and Groscurth, P. (1989). Use of fibrin glue as a substrate for in vitro endothelialization of PTFE vascular grafts. *Surgery* 105, 515-522.

We claim:

1. A method of treating a blood vessel defect in a subject in need thereof comprising implanting a vascular graft in the subject, wherein the vascular graft comprises (a) a polymeric substrate coated by an endothelial cell attachment agent while the polymeric substrate was in a de-gassed state and (b) human arterial endothelial cells adhered to the coated polymeric substrate.

2. The method of claim 1, wherein the vascular graft is implanted to replace a portion of a diseased or damaged blood vessel.

3. The method of claim 2, wherein the damaged blood vessel is a result of trauma.

4. The method of claim 2, wherein the diseased or damaged blood vessel is a result of vascular disease.

5. The method of claim 1, wherein the vascular graft is implanted by anastomosis.

6. The method of claim 1, wherein the human arterial endothelial cells have not been genetically modified to reduce rejection by the immune system.

7. A method of implanting a vascular graft in a subject in need thereof, wherein the vascular graft comprises (a) a polymeric substrate coated by an endothelial cell attachment agent while the polymeric substrate was in a de-gassed state and (b) human arterial endothelial cells adhered to the coated polymeric substrate.

8. The method of claim 7, wherein the vascular graft is implanted by anastomosis.

9. The method of claim 7, wherein the human arterial endothelial cells have not been genetically modified to reduce rejection by the immune system.

10. The method of claim 7, wherein the vascular graft is implanted during congenital heart surgery, coronary artery bypass surgery, or peripheral vascular surgery.

11. The method of claim 1, wherein the polymeric substrate is expanded polytetrafluoroethylene (ePTFE), poly vinyl chloride (PVC), PGA (poly glycolic acid), PLA (poly lactic acid), PCL (poly caprolactone), PGLA (polylactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracellular matrix protein-based scaffold, hyaluronic acid, chitosan, or polyhydroxyalkanoate.

12. The method of claim 7, wherein the polymeric substrate is expanded polytetrafluoroethylene (ePTFE), poly vinyl chloride (PVC), PGA (poly glycolic acid), PLA (poly lactic acid), PCL (poly caprolactone), PGLA (polylactic-co-glycolic acid), polyurethane, polydioxanone, polyethylene, polyethylene terephthalate (Dacron®), tetrafluoroethylene (TFE), polytetrafluoroethylene (PTFE), silk, decellularized scaffold, an extracellular matrix protein-based scaffold, hyaluronic acid, chitosan, or polyhydroxyalkanoate.

13. A method of treating a blood vessel defect in a subject in need thereof comprising implanting a vascular graft in a subject, wherein the vascular graft comprises (a) a polymeric substrate coated by an endothelial cell attachment agent while the polymeric substrate was in a de-gassed state and (b) non-major histocompatibility complex matched human arterial endothelial cells adhered to the coated, polymeric substrate.

* * * * *